US012576102B2

(12) United States Patent
Bowman et al.

(10) Patent No.: US 12,576,102 B2
(45) Date of Patent: Mar. 17, 2026

(54) METHODS FOR IDENTIFYING PRE-DISPOSITION TO COGNITIVE DECLINE AND AGENTS FOR REDUCING OR PREVENTING COGNITIVE DECLINE, OR IMPROVING COGNITIVE ABILITY

(71) Applicant: SOCIETE DES PRODUITS NESTLE S.A., Vevey (CH)

(72) Inventors: Gene Bowman, St-Sulpice (CH); Julie Hudry-Labbe, Epalinges (CH); Jeroen Antonius Johannes Schmitt, Moudon (CH); Corina Mudini, Lausanne (CH); Claus Rieker, Fribourg (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 18/120,189

(22) Filed: Mar. 10, 2023

(65) Prior Publication Data

US 2023/0226097 A1     Jul. 20, 2023

Related U.S. Application Data

(62) Division of application No. 16/603,688, filed as application No. PCT/EP2018/058701 on Apr. 5, 2018.

(60) Provisional application No. 62/484,119, filed on Apr. 11, 2017, provisional application No. 62/484,156, filed on Apr. 11, 2017.

(30) Foreign Application Priority Data

| | | |
|---|---|---|
| Sep. 29, 2017 | (EP) | .................................... 17193916 |
| Sep. 29, 2017 | (WO) | ................. PCT/EP2017/074731 |
| Dec. 11, 2017 | (WO) | ................. PCT/EP2017/082148 |

(51) Int. Cl.

| | |
|---|---|
| *A61K 31/714* | (2006.01) |
| *A61K 31/14* | (2006.01) |
| *A61K 31/198* | (2006.01) |
| *A61K 31/202* | (2006.01) |
| *A61K 31/592* | (2006.01) |
| *A61K 31/593* | (2006.01) |
| *A61P 25/28* | (2006.01) |
| *G01N 33/68* | (2006.01) |
| *G01N 33/82* | (2006.01) |

(52) U.S. Cl.
CPC ........... *A61K 31/714* (2013.01); *A61K 31/14* (2013.01); *A61K 31/198* (2013.01); *A61K 31/202* (2013.01); *A61K 31/592* (2013.01); *A61K 31/593* (2013.01); *A61P 25/28* (2018.01); *G01N 33/6896* (2013.01); *G01N 33/82* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 6,153,653 | A | 11/2000 | Shashoua |
| 6,790,462 | B2 | 9/2004 | Hendricks |
| 8,486,889 | B1 | 7/2013 | Petrus |
| 10,821,130 | B2 | 11/2020 | Silber et al. |
| 2002/0182196 | A1 | 12/2002 | Mccleary |
| 2007/0078114 | A1 | 4/2007 | Hobden et al. |
| 2008/0003330 | A1 | 1/2008 | Rueda et al. |
| 2011/0257109 | A1 | 10/2011 | Wurtman |
| 2012/0094315 | A1 | 4/2012 | Fryar-Williams |
| 2014/0004205 | A1 | 1/2014 | Satyaraj |
| 2014/0271844 | A1 | 9/2014 | Miller |
| 2015/0086625 | A1 | 3/2015 | Miller |
| 2015/0209306 | A1 | 7/2015 | Bredesen et al. |
| 2016/0038552 | A1 | 2/2016 | Bredesen et al. |
| 2018/0268940 | A1* | 9/2018 | Bredesen ............. A61B 5/4848 |
| 2020/0054665 | A1 | 2/2020 | Rieker et al. |

FOREIGN PATENT DOCUMENTS

| | | |
|---|---|---|
| CN | 101897706 A | 12/2010 |
| JP | 2010531351 A | 9/2010 |
| JP | 2017504808 | 2/2017 |
| JP | 2017504808 A | 2/2017 |
| WO | 0203074 | 1/2002 |
| WO | 2010143053 | 12/2010 |
| WO | 2011143587 | 11/2011 |
| WO | 2012049222 A2 | 4/2012 |
| WO | 2014122290 | 8/2014 |
| WO | 2015140545 | 9/2015 |

(Continued)

OTHER PUBLICATIONS

Nist. NIST Releases Vitamin D Standard Reference Material. Retrieved from the Internet on Sep. 26, 2023, https://www.nist.gov/news-events/news/2009/07/nist-releases-vitamin-d-standard-reference-material. Published 2009 (Year: 2009).*

MilliporeSigma. Automated assay for the determination of methylmalonic acid, total homocysteine. Retrieved from the Internet on Sep. 24, 2023, https://www.sigmaaldrich.com/US/en/tech-docs/paper/235961. Published 2005 (Year: 2005).*

PubChem. Cholecalciferol. Retrieved from the Internet on Sep. 26, 2023, https://pubchem.ncbi.nlm.nih.gov/compound/5280795 (Year: 2023).*

Chao Dou, Dongyuan Xia, Liqing Zhang, Xiaoru Chen, Patrick Flores, Abhijit Datta, Chong Yuan, Development of a Novel Enzymatic Cycling Assay for Total Homocysteine, Clinical Chemistry, vol. 51, Issue 10, Oct. 1, 2005, pp. 1987-1989 (Year: 2005).*

(Continued)

*Primary Examiner* — James H Alstrum-Acevedo
*Assistant Examiner* — Lauren Wells
(74) *Attorney, Agent, or Firm* — K&L Gates LLP

(57) ABSTRACT

A method for identifying pre-disposition to cognitive decline in a subject, the method comprising determining levels of: (a) omega-3 fatty acids, and vitamin D or a metabolite thereof; (b) omega-3 fatty acids, and homocysteine; (c) vitamin D or a metabolite thereof, and homocysteine; or (d) omega-3 fatty acids, vitamin D or a metabolite thereof, and homocysteine, independently in one or more samples obtained from the subject.

11 Claims, 3 Drawing Sheets

(56) References Cited

FOREIGN PATENT DOCUMENTS

| WO | 2016207794 | 12/2016 |
| WO | 2017004436 | 1/2017 |

OTHER PUBLICATIONS

NIH, National Cancer Institute. Composition of the Blood. Retrieved from the internet on Mar. 29, 2024, https://training.seer.cancer.gov/leukemia/anatomy/composition.html. (Year: 2024).*

Agilent. Determination of red blood cell fatty acid profiles in clinical research. Retrieved from the Internet on Mar. 29, 2024, file:///C:/Users/lwells/Downloads/AgilentO3FA.pdf. Published Mar. 8, 2018. (Year: 2018).*

Alina Health. Vitamin D 25 (Deficiency)-113A. Retrieved from the Internet on Mar. 29, 2024, https://labs.allinahealth.org/Lab/Preview?templateUID=ff24f908-cdc8-4068-84eb-6ce60783f288&customObjectUID=471552e4-9126-4cce-b080-7a6078f55726. Published 2007. (Year: 2007).*

PubChem. Cholecalciferol. Retrieved from the Internet on Apr. 19, 2024, https://pubchem.ncbi.nlm.nih.gov/compound/5280795. (Year: 2024).*

Harris, William. Achieving optimal n-3 fatty acid status: the vegetarian's challenge . . . or not, The American Jn of Clinical Nutrition, vol. 100, Supp. 1, Jul. 2014, pp. 449S-452S. (Year: 2014).*

Miller et al. Vitamin D Status and Rates of Cognitive Decline in a Multiethnic Cohort of Older Aduts, JAMA Neurol. 2015; 72(11):1295-1303. (Year: 2015).*

Ueland PM, Refsum H, Stabler SP, Malinow MR, Andersson A, Allen RH. Total homocysteine in plasma or serum: methods and clinical applications. Clin Chem. Sep. 1993;39(9):1764-79. (Year: 1993).*

Tan et al. Red blood cell omega-3 fatty acid levels and markers of accelerated brain again, Neurology, 78(9) 658-664, published Feb. 28, 2012. (Year: 2012).*

Dou et al. Development of a Novel Enzymatic Cycling Assay for Total Homocysteine, Abstracts of Oak Ridge Posters, Clinical Chemistry 51, No. 10, 2005. (Year: 2005).*

Schober et al. Determination of red blood cell fatty acid profiles: Rapid and high-confident analysis by chemical ionization-gas chromatography-tandem mass spectrometry. J Chromatogr B Analyt Technol Biomed Life Sci. Jan. 1, 2017;1040:1-7. (Year: 2017).*

Haan et al., "Homocysteine, B Vitamins, and the Incidence of Dementia and Cognitive Impairment: Results from the Sacramento Area Latino Study on Aging2", The American Journal of Clinical Nutrition, vol. 85, Issue No. 2, 2007, pp. 1-14.

Graaf et al., "Matching, an Appealing Method to Avoid Confounding?", Nephron Clinical Practice, vol. 118, Issue No. 4, 2011, pp. c315-c318.

Gillette-Guyonnet et al., "Nutrition and Neurodegeneration: Epidemiological Evidence and Challenges for Future Research", British Journal of Clinical Pharmacology, vol. 75, Issue No. 3, 2013, pp. 738-755.

Tucker, "Nutrient Intake, Nutritional Status, and Cognitive Function with Aging", Annals of the New York Academy of Sciences, vol. 1367, Issue No. 1, 2016, pp. 38-49.

Bowman et al., "Nutrient Biomarker Patterns and Cognitive Decline in Older Adults (124.6)" The Journal Federation of American Societes for Experimental Biology, vol. 28, Issue No. 1, Apr. 1, 2014, 2 Pages, XP009503473.

Chinese Office Action for Appl No. 201780087975.4 dated Dec. 13, 2023.

Bowman et al., "Nutrient Biomarker Patterns, Cognitive Function, and MRI Measures of Brain Aging", Neurology, vol. 78, Issue No. 4, Jan. 24, 2012, pp. 241-249.

Lee et al., "Nutritional Risk and Cognitive Impairment in the Elderly", Archives of Gerontology and Geriatrics, vol. 48, 2009, pp. 95-99.

Barberger-Gateau, P. "Nutrition and brain aging: how can we move ahead?" European Journal of Clinical Nutrition, 2014, vol. 68, pp. 1245-1249.

Bowman et al. "Nutrient biomarker patterns and cognitive decline in older adults" The FASEB Journal, Federation of American Societes for Experimental Biology, Mar. 31, 2014, vol. 28, No. 1, suppl. S, p. 124.6 , XP009503473.

Heude et al., "Cognitive Decline And Fatty Acid Composition Of Erythrocyte Membranes-The EVA Study1-4", The I American Journal of Clinical Nutrition, vol. 77, Issue No. 4, Apr. 1, 2003, pp. 803-808.

Wang et al., "Nutritional Biomarkers in Alzheimers Disease: The Association Between Carotenoids, n-3 Fatty Acids, and Dementia Severity", Journal of Alzheimers Disease, vol. 13, Issue No. 1, Feb. 25, 2008, pp. 31-38.

Hashimoto, "Omega-3 Fatty Acids and Cognition", Nihon Rinsho, Japanes Journal of Clinical Medicine, vol. 72, Issue No. 4, 2014, pp. 648-656.

Japan Patent Office Action communication for Application No. 2019-550821, mailed on Nov. 29, 2022, 8 pages.

Rose et al. Why Match? Investigating Matched Case-Control Study Designs with Causal Effect Estimation. The International Journal of Biostatistics. vol. 5, Issue 1, Published 2009. (Year: 2009).

Hiller et al., The Relationship Between Nutrient Status and Cognitive Performance in Persons with Parkinson's Disease (P5.357)}, Neurology, vol. 86, Issue No. 16, Retrieved from (http://n.neurology.org/content/86/16_Supplement/P5.357), Apr. 5, 2016, pp. 1-5.

Japan Patent pages Office Communication for Application No. P2019-551444, Dispatch No. 235461, Dispatch Date May 31, 2022, 9 pages.

Cyhlarova et al., "Membrane Fatty Acids, Reading and Spelling in Dyslexic and Non-Dyslexic Adults", European Neuropsychopharmacology, vol. 17, Issue No. 2, 2006, pp. 1-6.

Oulhaj et al., "Omega-3 Fatty Acid Status Enhances the Prevention of Cognitive Decline by B Vitamins in Mild Cognitive Impairment", Journal of Alzheimer's Disease, vol. 50, Issue No. 2, 2016, pp. 547-557.

Sindi et al., "The CAIDE Dementia Risk Score App: the Development of an Evidence-Based Mobile Application to Predict the Risk of Dementia," Alzheimer's & Dementia: Diagnosis, Assessment & Disease Monitoring, vol. 1, Issue No. 3, 2015, pp. 328-333.

Hughes et al., Vitamin B12 and Ageing: Current Issues and Interaction with Folate, Annals of Clinical Biochemistry, vol. 50, Issue No. 4, 2013, pp. 315-329.

Fallis. 18 Powerful Ways to Effectively Lower Homocysteine. Optimal Living Dynamics. Published Apr. 17, 2017. Retrieved from the internet on Jun. 7, 2022, https://www.optimallivingdynamics.com/blog/16-proven-ways-to-effectively-lower-homocysteine. (Year: 2017).

Singh et al., "Association of Vitamin D and Homocysteine Level in Angiographically Proven Coronary Heart Disease Patients", Journal of Family Medicine, vol. 2, Issue No. 2, 2015, pp. 1-6.

* cited by examiner

A

B

METHODS FOR IDENTIFYING PRE-DISPOSITION TO COGNITIVE DECLINE AND AGENTS FOR REDUCING OR PREVENTING COGNITIVE DECLINE, OR IMPROVING COGNITIVE ABILITY

CROSS REFERENCE TO RELATED APPLICATIONS

The present application is a divisional of U.S. patent application Ser. No. 16/603,688 filed Oct. 8, 2019, which is a National Stage of International Application No. PCT/EP2018/058701, filed on Apr. 5, 2018, which claims priority to U.S. Provisional Patent Application No. 62/484,119, filed on Apr. 11, 2017, U.S. Provisional Patent Application No. 62/484,156, filed on Apr. 11, 2017, European Patent Application No. 17193916.8, filed on Sep. 29, 2017, International Application No. PCT/EP2017/074731, filed on Sep. 29, 2017, U.S. Provisional Patent Application No. 62/580,574, filed on Nov. 2, 2017, and International Application No. PCT/EP2017/082148, filed on Dec. 11, 2017, the entire contents of which are being incorporated herein by reference.

FIELD OF THE INVENTION

The present invention relates to methods for identifying pre-disposition to cognitive decline in subjects, and agents for reducing or preventing cognitive decline, or improving cognitive ability, in particular reducing or preventing cognitive decline, or improving cognitive ability in subjects identified according to a method of the invention.

BACKGROUND TO THE INVENTION

Population ageing has been a remarkable demographic event. As the growth of the older population has outpaced the total population due to increased longevity, the proportion of older persons relative to the rest of the population has increased considerably due to decreased fertility rates. For example, one in every twelve individuals was at least 60 years of age in 1950, and one in every ten was aged 60 years or older by the end of 2000. By the end of 2050, the number of persons worldwide that are 60 years or over is projected to be one in every five.

Aged or ageing individuals frequently suffer some degree of cognitive impairment, including decline in cognitive function that progresses with age and age-related changes in brain morphology and cerebrovascular function are commonly observed. Cognitive decline has been consistently reported with ageing across a range of cognitive domains including processing speed, attention, episodic memory, spatial ability and executive function. Brain imaging studies have revealed that these normal age-related cognitive declines are associated with decreases in both grey and white matter volume in the brain, with the fronto striatal system most heavily compromised with ageing. These decreases in cortical volume can be attributed to a number of detrimental cellular processes involved with normal ageing, such as accumulation of damage by free radicals over time leading to oxidative damage, chronic low-grade inflammation, homocysteine (Hey) accumulation, and decreased mitochondrial efficiency. In addition to direct cellular damage, the brain is also indirectly impaired by insults to micro-vascular structures. It is evident that the pathology of ageing and also dementia involves a complexity of these interacting factors, which are linked together. For example, mitochondrial dysfunction leads to increased oxidative stress, and oxidative stress can trigger inflammation and vascular insults.

Furthermore, cognitive decline is an early predictor for Alzheimer pathology and begins before the onset of dementia. In this context, the cognitive composite score represents a reliable means to assess the cognitive decline preceding dementia. Considerable evidence suggests that maintaining brain health and preventing cognitive decline with advancing age may prevent or delay development of dementia due to Alzheimer's disease and other age-related neuropathologies.

Nutrition, education, physical exercise and cognitive exercise have been recently demonstrated as possible interventions to prevent cognitive decline with ageing. An abundance of clinical, epidemiological and individual evidence is in favour of individual nutritional factors that reduce dementia risk and age-related neurodegeneration. However, formal trial testing of nutritional interventions has yielded mixed results (Schmitt et al. (2010) Nutrition Reviews 68: S2-S5).

Several long-term studies have failed to observe any cognitive benefits with interventions using combinations of B6, B12 and folate. McMahon et al. (2006) N Engl J Med 354(26): 2764-2772 found no effect on cognition in adults aged 65+ after 2 years consumption of a supplement containing folate (1000 μg), Vitamin B12 (500 μg) and B6 (10 mg). Similarly, Hankey et al. (2013) Stroke 44(8): 2232-2239 found that daily supplementation with folic acid (2000 μg), Vitamin B6 (25 mg) and Vitamin B12 (500 μg) to cognitively unimpaired patients with previous stroke or transient ischemic attack, lowered mean tHcy but had no effect on the incidence of cognitive impairment or cognitive decline, as measured by the Mini Mental State Examination (MMSE), during a median of 2.8 years.

Several short-term studies have also failed to show an effect of the combination of B6, B12 and folate for improving cognitive function. Lewerin et al. (2005) Am J Clin N utr 81 (5): 1155-1162, found that 4 months of supplementation of folic acid (800 μg), Vitamin B12 (500 μg) and Vitamin B6 (3 mg) had no effect on cognition in older adults (median age 76 years).

Accordingly, there remains a significant need for methods of reducing or preventing cognitive decline, or improving cognitive ability in subjects. Furthermore, there exists a need for identifying subjects who are pre-disposed to cognitive decline, for example to enable earlier intervention in those subjects to reduce the occurrence and/or extent of cognitive decline.

SUMMARY OF THE INVENTION

The inventors utilised banked bio-specimens originating from the Multi-domain Alzheimer Preventive Trial (MAPT; a study which was designed to assess the effects of an omega 3 2 supplement, a multi-domain intervention comprised of nutritional counselling, physical exercise and cognitive engagement, or a combination of the supplement and multi-domain intervention, versus a placebo in preventing cognitive decline in 1680 non-demented adults aged 70 and older) to quantify three biomarkers that represent distinct pathways toward cognitive decline and dementia. There biomarkers were: homocysteine as a marker of disturbed one carbon metabolism; 25-hydroxyvitamin D as a steroid hormone marker of disturbed vitamin D binding protein and receptor activity in the brain; and the omega 3 index indicative of fatty acid metabolism. The inventors found that each of these markers are independent risk factors for cognitive decline and that combined they compound the rate of cognitive decline.

Based on these findings, the inventors developed a "nutritional risk index" (NRI) based on omega-3 fatty acids, homocysteine and vitamin D levels, which identifies adults with distinct trajectories of cognitive decline, independent of age, gender, education, APOE4 genotype and intervention arms. Each point increase in the NRI is associated with more accelerated cognitive decline over 3 years. These data suggest that reducing nutritional risk attributable to low vitamin D3 and erythrocyte omega 3 fatty acids, and/or high homocysteine may reduce or prevent age-related cognitive decline, or improve cognitive ability.

Furthermore, the inventors believe that prior nutritional interventions attempting to reduce cognitive decline, dementia risk and age-related neurodegeneration have focused on the administration of nutrients in isolation rather than together intelligently in combination to increase the magnitude of effect through nutrient interaction. Moreover, studies investigating the effects of combined ingredients on cognitive function have used a mixture of constituents that all target the same mechanism (e.g. a mix of folate, and Vitamins B12 and B6 targeting Hcy levels, or a mix of Vitamins C and E targeting oxidative damage), which may be why that evidence is as inconsistent as the single ingredient research. In contrast, the present disclosure relates to a multi-intervention approach whereby each of the interventions targets a different risk factor associated with cognitive decline.

Accordingly, in one aspect the invention provides a method for identifying pre-disposition to cognitive decline in a subject, the method comprising determining levels of:

(a) omega-3 fatty acids, and vitamin D or a metabolite thereof;

(b) omega-3 fatty acids, and homocysteine;

(c) vitamin D or a metabolite thereof, and homocysteine; or (d) omega-3 fatty acids, vitamin D or a metabolite thereof, and homocysteine, independently in one or more samples obtained from the subject.

In one embodiment, the method comprises determining levels of omega-3 fatty acids, and vitamin D or a metabolite thereof. In one embodiment, the method comprises determining levels of omega-3 fatty acids, and homocysteine. In one embodiment, the method comprises determining levels of vitamin D or a metabolite thereof, and homocysteine.

In a preferred embodiment, the method comprises determining levels of omega-3 fatty acids, vitamin D or a metabolite thereof, and homocysteine.

In one embodiment, the method comprises:

(a) determining the level of two or more of omega-3 fatty acids, vitamin D or a metabolite thereof, or homocysteine independently in one or more samples obtained from the subject; and (b) comparing the levels of the two or more of omega-3 fatty acids, vitamin D or a metabolite thereof, or homocysteine to two or more reference values, wherein the levels of the two or more of omega-3 fatty acids, vitamin D or a metabolite thereof, or homocysteine compared to the two or more reference values is indicative of pre-disposition to cognitive decline in the subject.

In one embodiment:

(a) a level of omega-3 fatty acids is determined and a decrease in the level of omega-3 fatty acids in the sample from the subject compared to a reference value is indicative of pre-disposition to cognitive decline;

(b) a level of vitamin D or a metabolite thereof is determined and a decrease in the level of vitamin D or metabolite thereof in the sample from the subject compared to a reference value is indicative of pre-disposition to cognitive decline; and/or (c) a level of homocysteine is determined and an increase in the level of homocysteine in the sample from the subject compared to a reference value is indicative of pre-disposition to cognitive decline.

In one embodiment, the one or more samples are independently selected from the group consisting of a blood sample, plasma sample and serum sample.

In one embodiment, the level of omega-3 fatty acids is determined in a blood sample, preferably an erythrocyte sample. In one embodiment, the level of vitamin D or metabolite thereof is determined in a serum sample. In one embodiment, the level of homocysteine is determined in a plasma sample.

In one embodiment, the omega-3 fatty acid is eicosapentaenoic acid (EPA) and/or docosahexaenoic acid (DHA). In a preferred embodiment, the omega-3 fatty acid is erythrocyte membrane EPA and/or erythrocyte membrane DHA.

In one embodiment, the omega-3 fatty acid is EPA. In one embodiment, the omega-3 fatty acid is DHA. In one embodiment, the omega-3 fatty acid is EPA and DHA. In a preferred embodiment, the omega-3 fatty acid is erythrocyte membrane EPA. In a preferred embodiment, the omega-3 fatty acid is erythrocyte membrane DHA. In a particularly preferred embodiment, the omega-3 fatty acid is erythrocyte membrane EPA and erythrocyte membrane DHA.

In one embodiment, the vitamin D or metabolite thereof is vitamin D3, vitamin D2, 25-hydroxyvitamin D3 and/or 25-hydroxyvitamin D2.

In one embodiment, the vitamin D or metabolite thereof is vitamin D3. In one embodiment, the vitamin D or metabolite thereof is vitamin D2. In one embodiment, the vitamin D or metabolite thereof is 25-hydroxyvitamin D3. In one embodiment, the vitamin D or metabolite thereof is 25-hydroxyvitamin D2.

In a preferred embodiment, the vitamin D or metabolite thereof is 25-hydroxyvitamin D. In a preferred embodiment, the vitamin D or metabolite thereof is 25-hydroxyvitamin D3 and 25-hydroxyvitamin D2.

In one embodiment, the omega 3 fatty acid level in the sample is measured using gas chromatography. In one embodiment, the vitamin D or a metabolite thereof level in the sample is measured using an electrochemiluminescence binding assay. In one embodiment, the homocysteine level in the sample is measured using an enzymatic cycling assay.

In one embodiment, the subject is a human subject.

In one embodiment, the subject is an ageing human subject. In one embodiment, the subject is a human subject of at least 50, 55, 60, 65, 70, 75, 80, 85, 90 or 95 years of age. In a preferred embodiment, the subject is a human subject of 50 years of age or more. In a particularly preferred embodiment, the subject is a human subject of 70 years of age or more.

In one embodiment, the subject does not have dementia.

In one embodiment, the subject has a Clinical Dementia Rating (CDR) of 0.5 at baseline.

In one embodiment, the subject has a risk score in Cardiovascular Risk Factors, Aging and Dementia (CAIDE) of 10 to 15 at baseline.

In one embodiment, the subject is amyloid positive on amyloid PET scans at baseline.

In one embodiment, the subject has a genotype indicating risk of cognitive decline. In one embodiment, the subject is an APOE4 carrier.

In another embodiment, the subject is at risk of dementia determined by one or more risk factors selected from the group consisting of age, vascular risk factors (e.g. hypertension and/or diabetes), APOE4 genotype, amyloid positive (e.g. on amyloid PET scans), presence of white matter lesions, other signs of cerebral small vessel disease (e.g. infarcts and/or lacunes) and depression.

In one embodiment, the method further comprises combining the level of the omega-3 fatty acids, vitamin D or a metabolite thereof, and/or homocysteine with one or more anthropometric measures and/or lifestyle characteristics of the subject. Preferably, the anthropometric measure is selected from the group consisting of gender, weight, height, age and body mass index. Preferably, the lifestyle characteristic is whether the subject is a smoker or a non-smoker.

In one embodiment, the method further comprises combining the level of the omega-3 fatty acids, vitamin D or a metabolite thereof, and/or homocysteine with the gender of the subject.

In one embodiment, the method further comprises combining the level of the omega-3 fatty acids, vitamin D or a metabolite thereof, and/or homocysteine with the age of the subject.

Preferably, the method is an in vitro method.

In another aspect, the invention provides an omega-3 fatty acid for use in reducing or preventing cognitive decline, or improving cognitive ability in a subject, wherein the omega-3 6 fatty acid is administered to the subject simultaneously, sequentially or separately with vitamin D or a metabolite thereof, and/or an agent capable of reducing plasma homocysteine levels.

In one embodiment, the omega-3 fatty acid is administered to the subject simultaneously, sequentially or separately with vitamin D or a metabolite thereof. In one embodiment, the omega-3 fatty acid is administered to the subject simultaneously, sequentially or separately with an agent capable of reducing plasma homocysteine levels. In a preferred embodiment, the omega-3 fatty acid is administered to the subject simultaneously, sequentially or separately with vitamin D or a metabolite thereof, and an agent capable of reducing plasma homocysteine levels.

In another aspect, the invention provides vitamin D or a metabolite thereof for use in reducing or preventing cognitive decline, or improving cognitive ability in a subject, wherein the vitamin D or metabolite thereof is administered to the subject simultaneously, sequentially or separately with an omega-3 fatty acid, and/or an agent capable of reducing plasma homocysteine levels.

In one embodiment, the vitamin D or a metabolite thereof is administered to the subject simultaneously, sequentially or separately with an omega-3 fatty acid. In one embodiment, the vitamin D or a metabolite thereof is administered to the subject simultaneously, sequentially or separately with an agent capable of reducing plasma homocysteine levels. In a preferred embodiment, the vitamin D or a metabolite thereof is administered to the subject simultaneously, sequentially or separately with an omega-3 fatty acid, and an agent capable of reducing plasma homocysteine levels.

In another aspect, the invention provides an agent capable of reducing plasma homocysteine levels for use in reducing or preventing cognitive decline, or improving cognitive ability in a subject, wherein the agent capable of reducing plasma homocysteine levels is administered to the subject simultaneously, sequentially or separately with an omega-3 fatty acid, and/or vitamin D or a metabolite thereof.

In one embodiment, the agent capable of reducing plasma homocysteine levels is administered to the subject simultaneously, sequentially or separately with an omega-3 fatty acid. In one embodiment, the agent capable of reducing plasma homocysteine levels is administered to the subject simultaneously, sequentially or separately with vitamin D or a metabolite thereof. In a preferred embodiment, the agent capable of reducing plasma homocysteine levels is administered to the subject simultaneously, sequentially or separately with an omega-3 fatty acid, and vitamin D or a metabolite thereof.

In another aspect, the invention provides a combination of (a) an omega-3 fatty acid; (b) vitamin D or a metabolite thereof; and (c) an agent capable of reducing plasma homocysteine levels for use in reducing or preventing cognitive decline, or improving cognitive ability in a subject, wherein (a), (b) and (c) are administered to the subject simultaneously, sequentially or separately.

In another aspect, the invention provides a method for reducing or preventing cognitive decline, or improving cognitive ability in a subject comprising administering:
  (a) an omega-3 fatty acid, and vitamin D or a metabolite thereof;
  (b) an omega-3 fatty acid, and an agent capable of reducing plasma homocysteine levels;
  (c) vitamin D or a metabolite thereof, and an agent capable of reducing plasma homocysteine levels; or
  (d) an omega-3 fatty acid, vitamin D or a metabolite thereof, and an agent capable of reducing plasma homocysteine levels,
to the subject.

In one embodiment, the use or method is for reducing or preventing cognitive decline in a subject. In another embodiment, the use or method is for improving cognitive ability in a subject.

In a preferred embodiment, the method comprises administering an omega-3 fatty acid, vitamin D or a metabolite thereof, and an agent capable of reducing plasma homocysteine levels to the subject.

In one embodiment, the subject is a subject identified as pre-disposed to cognitive decline by a method of the invention.

In one embodiment, the omega-3 fatty acid is eicosapentaenoic acid (EPA) and/or docosahexaenoic acid (DHA).

In one embodiment, the omega-3 fatty acid is EPA. In one embodiment, the omega-3 fatty acid is DHA. In one embodiment, the omega-3 fatty acid is EPA and DHA.

In one embodiment, the vitamin D or metabolite thereof is vitamin D3, vitamin D2, 25-hydroxyvitamin D3 and/or 25-hydroxyvitamin D2.

In one embodiment, the vitamin D or metabolite thereof is vitamin D3. In one embodiment, the vitamin D or metabolite thereof is vitamin D2. In one embodiment, the vitamin D or metabolite thereof is 25-hydroxyvitamin D3. In one embodiment, the vitamin D or metabolite thereof is 25-hydroxyvitamin D2.

In one embodiment, the vitamin D or metabolite thereof is 25-hydroxyvitamin D. In one embodiment, the vitamin D or metabolite thereof is 25-hydroxyvitamin D3 and 25-hydroxyvitamin D2.

In one embodiment, the agent capable of reducing plasma homocysteine levels is vitamin B6 and/or vitamin B9.

In one embodiment, the agent capable of reducing plasma homocysteine levels is vitamin B6. In one embodiment, the agent capable of reducing plasma homocysteine levels is vitamin B9. In one embodiment, the agent capable of reducing plasma homocysteine levels is vitamin B6 and vitamin B9.

In another embodiment, the agent capable of reducing plasma homocysteine levels is betaine (trimethylglycine).

In one embodiment, the subject is not administered a nitric oxide releasing compound.

In one embodiment, the omega-3 fatty acid, vitamin D or a metabolite thereof and/or agent capable of reducing plasma homocysteine levels is not administered to the subject simultaneously, sequentially or separately with a nitric oxide releasing compound.

In one embodiment, the subject is a human subject.

In one embodiment, the subject is an ageing human subject. In one embodiment, the subject is a human subject of at least 50, 55, 60, 65, 70, 75, 80, 85, 90 or 95 years of age. In a preferred embodiment, the subject is a human subject of 50 years of age or more. In a particularly preferred embodiment, the subject is a human subject of 70 years of age or more.

In one embodiment, the subject does not have dementia.

In one embodiment, the subject has a Clinical Dementia Rating (CDR) of 0.5 at baseline.

In one embodiment, the subject has a risk score in Cardiovascular Risk Factors, Aging and Dementia (CAIDE) of 10 to 15 at baseline.

In one embodiment, the subject is amyloid positive on amyloid PET scans at baseline.

In one embodiment, the subject has a genotype indicating risk of cognitive decline. In one embodiment, the subject is an APOE4 carrier.

In another embodiment, the subject is at risk of dementia determined by one or more risk factors selected from the group consisting of age, vascular risk factors (e.g. hypertension and/or diabetes), APOE4 genotype, amyloid positive (e.g. on amyloid PET scans), presence of white matter lesions, other signs of cerebral small vessel disease (e.g. infarcts and/or lacunes) and depression.

In one embodiment, the administration is a dietary intervention.

In one embodiment, the omega-3 fatty acid, vitamin D or a metabolite thereof and/or agent capable of reducing plasma homocysteine levels is orally administered to the subject daily for at least one month.

In one embodiment, the subject is further administered one or more B vitamins selected from the group consisting of Vitamin B1, Vitamin B2, Vitamin B3, Vitamin B5, Vitamin B7 and Vitamin B12.

In a preferred embodiment, the subject is further administered Vitamin B12.

In a preferred embodiment, the agent capable of reducing plasma homocysteine levels is vitamin B6 and the subject is further administered vitamin B12.

In one embodiment, the subject is administered an omega-3 fatty acid, vitamin D or a metabolite thereof, an agent capable of reducing plasma homocysteine levels and vitamin B12, wherein the agent capable of reducing plasma homocysteine levels is vitamin B6.

In one embodiment, the vitamin B12 is administered at a dosage of 0.1 to 40 times the RDA of vitamin B12 per day, preferably 10 to 40, 10 to 30 or 10 to 25 times the RDA of vitamin B12 per day, more preferably 12 to 21 times the RDA of vitamin B12 per day.

In one embodiment, the omega-3 fatty acid; vitamin D or a metabolite thereof; and/or agent capable of reducing plasma homocysteine levels are administered to the subject simultaneously, sequentially or separately with vitamin B12, wherein the vitamin B12 is administered at a dosage of 0.1 to 40 times the RDA of vitamin B12 per day, preferably 10 to 40, 10 to 30 or 10 to 25 times the RDA of vitamin B12 per day, more preferably 12 to 21 times the RDA of vitamin B12 per day.

In another embodiment, the omega-3 fatty acid; vitamin Dora metabolite thereof; and/or agent capable of reducing plasma homocysteine levels are administered to the subject simultaneously, sequentially or separately with vitamin B12, wherein the vitamin B12 is administered at a dosage of 50 to 500 times the RDA of Vitamin B12 per day, preferably a dosage of 100 to 300 times the RDA of Vitamin B12 per day, more preferably a dosage of 150 to 250 times the RDA of Vitamin B12 per day, for example about 200 times the RDA of Vitamin B12 per day.

In one embodiment, the subject is further administered one or more antioxidants selected from the group consisting of Vitamin C, Vitamin D, Vitamin E and selenium.

In one embodiment, the use or method of the invention reduces or prevents decline in memory and/or learning.

In one embodiment, the use or method of the invention improves memory and/or learning.

In one embodiment, the use or method of the invention provides an improvement of neuronal fluidity, stimulation of neuronal plasticity and activity, improvement of the anti-inflammatory potential, support or maintenance of cognitive performance, support or maintenance of brain performance, slowing down ageing of the brain, support of an active mind and brain fitness, support or maintenance of a healthy brain, enhancement of memory, enhancement of executive functions, enhancement of attention, maintenance of cognitive health and/or maintenance of brain cellular health.

In one embodiment, the omega-3 fatty acid, vitamin D or a metabolite thereof and/or agent capable of reducing plasma homocysteine levels is in the form of a food product, preferably further comprising an ingredient selected from the group consisting of protein, carbohydrate, fat and combinations thereof.

In one embodiment, the omega-3 fatty acid, vitamin D or a metabolite thereof and/or agent capable of reducing plasma homocysteine levels is in the form of a pharmaceutical composition further comprising a pharmaceutically acceptable carrier, diluent or excipient.

In another aspect, the invention provides a method of achieving one or more benefits selected from the group consisting of decreasing brain atrophy, increasing or maintaining number of synapses, increasing or maintaining amyloid-β phagocytosis and decreasing neuroinflammation in a subject in need thereof, the method comprising administering:

(a) an omega-3 fatty acid, and vitamin D or a metabolite thereof;

(b) an omega-3 fatty acid, and an agent capable of reducing plasma homocysteine levels;

(c) vitamin D or a metabolite thereof, and an agent capable of reducing plasma homocysteine levels; or (d) an omega-3 fatty acid, vitamin D or a metabolite thereof, and an agent capable of reducing plasma homocysteine levels, to the subject.

In a preferred embodiment, the method comprises administering an omega-3 fatty acid, vitamin D or a metabolite thereof, and an agent capable of reducing plasma homocysteine levels to the subject.

In another aspect, the invention provides a method of reducing or preventing dementia in a subject at risk thereof, the method comprising administering: to the subject a therapeutically effective amount of a composition comprising an omega-3 fatty acid, Vitamin B6 and Vitamin B9.

(a) an omega-3 fatty acid, and vitamin D or a metabolite thereof;

(b) an omega-3 fatty acid, and an agent capable of reducing plasma homocysteine levels;

(c) vitamin D or a metabolite thereof, and an agent capable of reducing plasma homocysteine levels; or (d) an omega-3 fatty acid, vitamin D or a metabolite thereof, and an agent capable of reducing plasma homocysteine levels, to the subject.

In a preferred embodiment, the method comprises administering an omega-3 fatty acid, vitamin D or a metabolite thereof, and an agent capable of reducing plasma homocysteine levels to the subject.

In one embodiment, the dementia is selected from the group consisting of Alzheimer's disease, vascular dementia, Lewy body dementia, frontotemporal dementia and combinations thereof.

In another aspect, the invention provides a method of improving cognitive ability in a subject, the method comprising administering:

(a) an omega-3 fatty acid, and vitamin D or a metabolite thereof;

(b) an omega-3 fatty acid, and an agent capable of reducing plasma homocysteine levels;

(c) vitamin D or a metabolite thereof, and an agent capable of reducing plasma homocysteine levels; or (d) an omega-3 fatty acid, vitamin D or a metabolite thereof, and an agent capable of reducing plasma homocysteine levels, to the subject.

In a preferred embodiment, the method comprises administering an omega-3 fatty acid, vitamin D or a metabolite thereof, and an agent capable of reducing plasma homocysteine levels to the subject.

In one embodiment, the subject does not have dementia.

In another aspect, the invention provides a method of selecting a modification in lifestyle of a subject comprising the steps:

(a) determining whether the subject is pre-disposed to cognitive decline according to the method of the invention; and (b) selecting a modification in lifestyle capable of preventing or reducing cognitive decline, or improving cognitive ability in a subject identified to be in need thereof.

In one embodiment, the method further comprises applying the selected modification in lifestyle to the subject.

In one embodiment, the modification in lifestyle comprises administering:

(a) an omega-3 fatty acid, and vitamin D or a metabolite thereof;

(b) an omega-3 fatty acid, and an agent capable of reducing plasma homocysteine levels;

(c) vitamin D or a metabolite thereof, and an agent capable of reducing plasma homocysteine levels; or (d) an omega-3 fatty acid, vitamin D or a metabolite thereof, and an agent capable of reducing plasma homocysteine levels, to the subject.

In a preferred embodiment, the method comprises administering an omega-3 fatty acid, vitamin D or a metabolite thereof, and an agent capable of reducing plasma homocysteine levels to the subject.

In another aspect, the invention provides a computer program product comprising computer implementable instructions for causing a programmable computer to determine whether a subject is pre-disposed to cognitive decline according to the method disclosed herein.

In another aspect, the invention provides a computer program product comprising computer implementable instructions for causing a programmable computer to determine whether a subject is pre-disposed to cognitive decline given the levels of the omega-3 fatty acids, vitamin D or a metabolite thereof, and/or homocysteine from the user.

(A) Mean slope of change in cognitive composite Z score over 3 years as a function of the baseline Nutritional Risk Index in MAPT. The Nutritional Risk Index increases by one point for each of the following: RBC EPA+DHA≤4.82 wt. % of total; Serum vitamin D≤≤20 ng/mL; plasma homocysteine ≥14.

Figure 1:
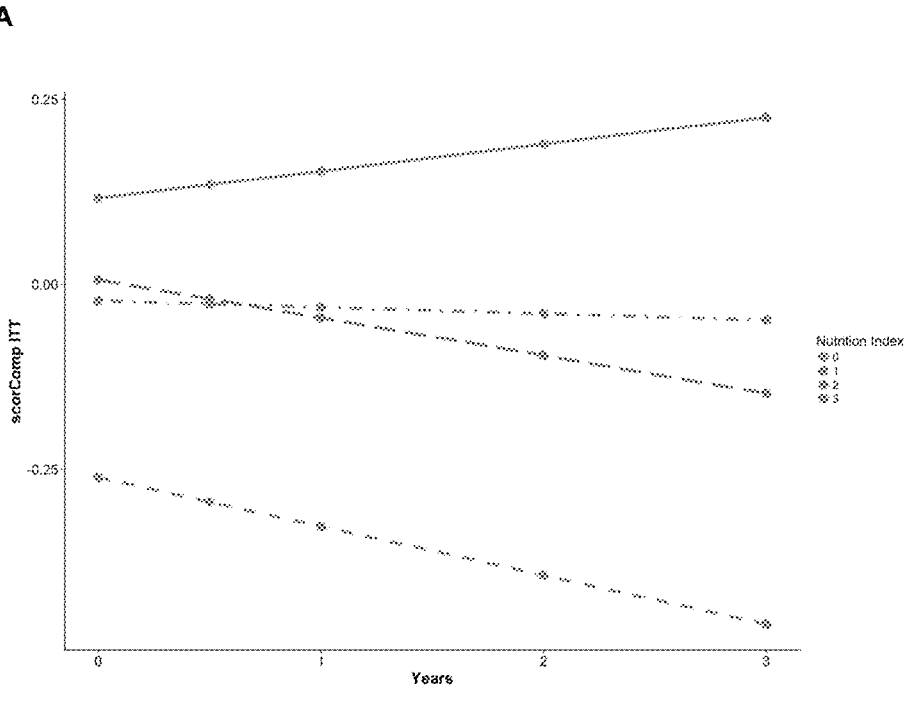
FIG. 1
Figure 1:
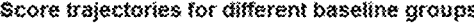
Figure 1:
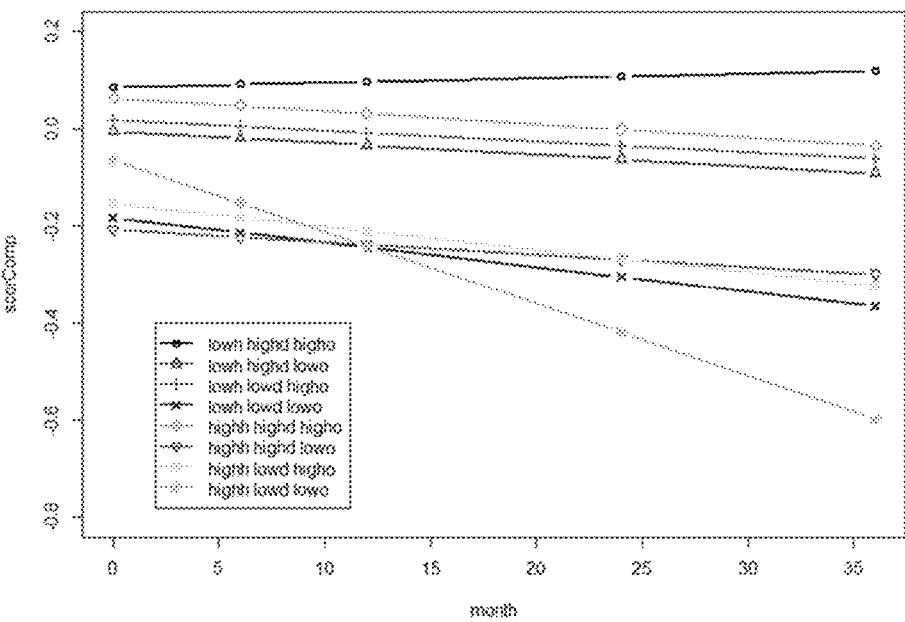

(B) Mean slope of change in cognitive composite Z score over 3 years as a function of each distinct nutritional risk profiles identified at baseline with the Nutritional Risk Index. FIG. 1B shows how rates of cognitive decline differ by Nutritional Risk Index (NRI) scores. Each subject is allocated a score of 0 or 1 depending on whether they meet the following criteria: Serum 25-hydroxyvitamin D≤20 ng/mL=1, otherwise 0; plasma homocysteine ≥14=1, otherwise 0; RBC omega 3≤4.82 wt. % of total=1, otherwise 0. Thus, each subject receives a NRI of 0-3, where NRI=3 is considered as highest nutritional risk for cognitive decline. Cognitive change is measured over four time points over 3 years.

The "lowh highd higho" line illustrates rates of cognitive decline in subjects with NRI=0. The "high highd higho", "lowh lowd higho" and "lowh highd lowo" lines illustrates rates of cognitive decline in subjects with NRI=1. The "high lowd higho", "lowh lowd lowo" and "high highd lowo" lines illustrate the rates of cognitive decline in subjects with NRI=2 and the "high lowd Iowa" line illustrates subjects with highest nutritional risk (NRI=3) and their rates of cognitive decline.

FIG. 2

Distribution and probability plots of vitamin D levels (ng/mL) in the subject population.

FIG. 3

Distribution and probability plots of homocysteine levels (μmol/L) in the subject population.

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

All percentages expressed herein are by weight of the total weight of the composition unless expressed otherwise.

The terms "food," "food product" and "food composition" as used herein mean a product or composition that is intended for ingestion by an individual, such as a human, and provides at least one nutrient to the individual. The compositions of the present disclosure, including the embodiments described herein, can comprise, consist of or consist essentially of the elements disclosed herein, as well as any additional or optional ingredients, components, or elements described herein or otherwise useful in a diet.

As used herein, an "effective amount" is an amount that prevents a deficiency, treats a disease or medical condition in an individual or, more generally, reduces symptoms, manages progression of the diseases or provides a nutritional, physiological, or medical benefit to the individual. The relative terms "improved," "increased," "enhanced" and the like refer to the effects of the composition disclosed herein relative to a composition lacking one or more ingredients and/or having a different amount of one or more ingredients, but otherwise identical.

Cognitive Decline and Ageing

The terms "cognition" and "cognitive ability" as used herein may mean the intellectual process by which an individual becomes aware of, perceives or comprehends ideas. Cognitive ability embraces the quality of knowing, which includes all aspects of perception, recognition, conception, sensing, thinking, reasoning, remembering and imaging. Loss of cognitive ability is the difficulty in dealing with or reacting to new information or situations. Cognitive decline or impairment may manifest itself in many ways, e.g. short-term memory loss, diminished capacity to learn, diminished rate of learning, diminished attention, diminished motor performance and/or dementia, among other indicia. Non-limiting examples of specific cognitive domains that include abilities that decrease with age are (i) attention: processing speed, and selected and divided attention; (ii) learning and memory: delayed free recall, source memory, prospective memory and episodic memory; (iii) language: verbal fluency, visitation naming and word finding; (iv) visuospatial abilities: visual construction skills; and (v) executive functioning: planning, decision making, reasoning and mental flexibility.

The terms "cognitive ageing" and "age-related cognitive decline" as used herein mean a decline in cognitive ability that progresses with age, for example an elderly age that is increasing, and can include age-related changes in brain morphology and/or cerebrovascular function. Cognitive ageing does not include impaired cognitive ability caused by an underlying condition other than ageing, such as a head injury or depression.

Levels of and improvements in cognition can be readily assessed by the skilled person using any suitable neurological and cognitive tests that are known in the art, including cognitive tests designed to assess speed of information processing, executive function and memory. Suitable example tests include Mini Mental State Examination (MMSE), Cambridge Neuropsychological Test Automated Battery (CANTAB), Alzheimer's Disease Assessment Scale-cognitive test (ADAScog), Wisconsin Card Sorting Test, Verbal and Figural Fluency Test and Trail Making Test, electroencephalography (EEG), magnetoencephalography (MEG), Positron Emission Tomography (PET), Single Photon Emission Computed Tomography (SPECT), Magnetic Resonance Imaging (MRI), functional Magnetic Resonance Imaging (fMRI), computerised tomography and long-term potentiation.

EEG, a measure of electrical activity of the brain, is accomplished by placing electrodes on the scalp at various landmarks and recording greatly amplified brain signals. MEG is similar to EEG in that it measures the magnetic fields that are linked to electrical fields. MEG is used to measure spontaneous brain activity, including synchronous waves in the nervous system.

PET provides a measure of oxygen utilisation and glucose metabolism. In this technique, a radioactive positron-emitting tracer is administered, and tracer uptake by the brain is correlated with brain activity. These tracers emit gamma rays which are detected by sensors surrounding the head, resulting in a 3D map of brain activation. As soon as the tracer is taken up by the brain, the detected radioactivity occurs as a function of regional cerebral blood flow. During activation, an increase in cerebral blood flow and neuronal glucose metabolism can be detected within seconds.

Suitable analysis can also be based on neuropsychiatric testing, clinical examinations and individual complaints of loss of cognitive function (e.g. subjective memory loss).

Cognitive decline may be, for example, interpreted as a statistically significant difference from the baseline performance in a suitable test.

A "non-demented" individual (also referred to herein as a subject "that does not have dementia") has a Clinical Dementia Rating of up to 0.5. The CDR measures dementia severity and is a global rating of dementia with scores ranging from 0 to 3 (0, 0.5, 1, 2 and 3) rated by a semi-structured subject and informant interview (Hughes et al. (1982) Br. J. Psychiatry 140: 566-72). A clinician synthesises the cognitive and functional abilities based on six domains, including memory, orientation, judgment and problem solving, community affairs, home and hobbies, and personal care. The scale has good inter-rater agreement.

The non-demented individual does not have any of Alzheimer's disease, vascular dementia, Lewy body dementia or frontotemporal dementia. In some embodiments, the non-demented individual is a healthy ageing individual. In other embodiments, the non-demented individual has a phenotype associated with age-related cognitive impairment. For example, when compared to a control individual not having the phenotype, the non-demented individual may have a phenotype that includes one or more of decreased ability to recall, short-term memory loss, decreased learning rate, decreased capacity for learning, decreased problem solving skills, decreased attention span, decreased motor performance or increased confusion.

A non-limiting example of a non-demented individual at risk of cognitive ageing is a human with spontaneous memory complaints, but who nevertheless has a Mini Mental State Examination (MMSE) score of at least 24 and has independence in basic daily activities as shown by an Activities of Daily Living (ADL) score of at least 4. An MMSE score for the present purpose may be e.g. 24 to 30, more preferably 26 to 30.

The MMSE is a very brief, easily administered/executed mental status examination that has proved to be a highly reliable and valid instrument for detecting and tracking the progression of the cognitive impairment associated with neurodegenerative diseases. The MMSE is a fully structured scale that consists of 30 points grouped into seven categories: orientation to place (state, county, town, hospital and floor), orientation to time (year, season, month, day and date), registration (immediately repeating three words), attention and concentration (serially subtracting 7, beginning with 100, or, alternatively, spelling the word world backward), recall (recalling the previously repeated three words), language (naming two items, repeating a phrase, reading aloud and understanding a sentence, writing a sentence and following a three-step command), and visual construction (copying a design) (Folstein et al. (1975) J. Psychiat. Res. 12: 189-198).

The MMSE is scored in terms of the number of correctly completed items; lower scores indicate poorer performance and greater cognitive impairment. The total score ranges from 0 to 30.

The ADL is an informant-based activity of daily living scale widely used measure to assess activities of daily living in people with and without AD. The instrument assesses ability over a wide range of performances. The ADL has shown sensitivity to change among mildly impaired individuals compared to non-impaired controls and can capture functional changes (Galasko et al. (1997) Alzheimer Dis. Assoc. Disord. 11 Suppl. 2: S33-9).

As noted earlier herein, considerable evidence suggests that maintaining brain health and preventing cognitive decline with advancing age may prevent or delay development of dementia. Therefore, the methods disclosed herein which prevent or reduce cognitive decline or ageing can also ultimately prevent dementia such as Alzheimer's disease. Accordingly, another aspect of the present disclosure is a method of preventing dementia in an individual at risk thereof. The method comprises administering to the individual a therapeutically effective amount of the compositions disclosed herein. The dementia that is prevented can be selected from the group consisting of Alzheimer's disease, vascular dementia, Lewy body dementia, frontotemporal dementia and combinations thereof.

Alzheimer's Disease

Alzheimer's disease is caused by atrophy of areas of the brain. Although it is not known what initiates the atrophy, studies have found amyloid plaques, neurofibrillary tangles and acetylcholine imbalances in the brains of Alzheimer's patients. Vascular damage in the brain, which may damage healthy neurons, is also common in Alzheimer's patients.

Alzheimer's disease is a progressive condition that affects multiple brain functions. Early signs of the disease usually include minor memory problems, for example forgetting recent events or the names of places and objects. As the disease progresses, memory problems become more severe and additional symptoms can develop, such as confusion, disorientation, difficulty making decisions, problems with speech and language, and personality changes.

Vascular Dementia

Vascular dementia results from reduced blood flow to the brain, which damages brain cells. The reduced blood flow can occur for a number of reasons, including narrowing of the blood vessels in the brain (subcortical vascular dementia), stroke (single-infarct dementia) and numerous small strokes (multi-infarct dementia). The reduced blood flow may additionally be caused by Alzheimer's disease, a combination referred to as mixed dementia.

Early symptoms of vascular dementia include slowness of thought, difficulty with planning, difficulty with language, problems with attention and concentration, and behavioural changes.

The symptoms typically worsen in steps, with intervening stable periods of months or years.

Parkinson's Disease

Parkinson's disease is a condition in which nerve cells in the substantia nigra become progressively damaged. Nerve cells in this area of the brain produce dopamine, which acts as a messenger between the parts of the brain and nervous system that control body movement.

Damage to these nerve cells results in a reduction in the amount of dopamine produced in the brain, which has the effect of reducing function in the part of the brain controlling movement.

Symptoms of the Parkinson's disease include tremors, slow movement, and stiff and inflexible muscles. Parkinson's disease patients may also experience additional symptoms, including depression, constipation, insomnia, anosmia and memory problems.

Determining Biomarker Levels

The level of the individual biomarker species in the sample may be measured or determined by any suitable method known in the art. For example, mass spectrometry (MS), antibody-based detection methods (e.g. enzyme-linked immunosorbent assay, ELISA), non-antibody protein scaffold-based methods (e.g. fibronectin scaffolds), radioimmunoassays (RIA) or aptamer-based methods may be used. Other spectroscopic methods, chromatographic methods, labelling techniques or quantitative chemical methods may also be used.

Suitable example methods to determine individual biomarker levels are described below.

25-Hydroxyvitamin D

Electrochemiluminescence binding assays may be utilised for the in vitro determination of total 25-hydroxyvitamin D (e.g. using the commercially available Cobas 8000, Roche). For example, Vitamin D-binding protein (VDBP) may be employed to capture both 25-hydroxyvitamin D3 and D2 with the intention to quantify total vitamin D. Briefly, the sample may be incubated with a pre-treatment reagent to denature the natural VDBP in the sample to release the bound vitamin D. The sample may then be further incubated with a recombinant ruthenium-labelled VDBP to form a complex of 25-hydroxyvitamin D (25-OH-D) and the ruthenylated-VDBP. Addition of a biotinylated 25-OH-D creates a complex consisting of the ruthenium-labelled VDBP and the biotinylated 25-0H-D. The entire complex may be bound to a solid phase by the interaction of biotin and streptavidin-coated microparticles, which may be captured on the surface of an electrode. After removal of unbound substances, adding voltage to the electrode induces chemiluminescent emission which may be measured by a photomultiplier. Results may be determined via an instrument-specific calibration curve.

Homocysteine

Total plasma homocysteine may be measured using an enzymatic cycling assay. Briefly, oxidised homocysteine may be first reduced and then reacted with S-adenosylmethionine to form methionine and S-adenosyl homocysteine (SAH) in the presence of homocysteine S-methyl transferase. SAH may then be assessed by coupled enzyme reactions where SAH is hydrolysed into adenosine and homocysteine by SAH hydrolase and homocysteine is cycled back into the homocysteine conversion reaction, which serves to amplify the detection signal. The formed adenosine may be hydrolysed into inosine and ammonia, and glutamate dehydrogenase may then be used to catalyse the reaction of ammonia with 2-oxoglutarate and NADH to form NAD+. The concentration of homocysteine in the sample is directly proportional to the amount of NADH converted to NAD+, which may be measured spectroscopically at an absorbance of 340 nm.

Omega 3 Fatty Acids

Omega 3 fatty acids such as EPA and DHA, for example expressed as a weight percentage of total fatty acids, may be quantified using gas chromatography coupled with a flame ionisation detector. Briefly, erythrocytes may be separated from plasma by centrifugation and washed before lipid extraction by the Folch method including a mixture of hexane and isopropanol after acidification. Margaric acid may be added as an internal standard. Total lipid extracts may then be saponified and methylated, and fatty acid methyl esters (FAME) may be extracted with pentane and analysed by gas chromatography (GC). An example protocol may use a gas chromatograph with a split injector, a bonded silica capillary column (BPX 70, 60 m×0.25 mm; 0.25 µm film thickness) and a flame ionisation detector; helium may be used as a carrier gas; and the column temperature program may be started at 150° C., increased by 1.3° C./min to 220° C. and held at 220° C. for 10 min. Identification of FAME may be based on retention times obtained for FAME prepared from fatty acid standards.

Samples

The invention comprises a step of determining the level of two or more biomarkers in one or more samples obtained from a subject.

In one embodiment, the one or more samples are independently selected from the group consisting of a blood sample, plasma sample and serum sample.

Techniques for collecting samples from a subject are well known in the art.

Comparison to Reference Values

The present method may comprise a step of comparing the levels of omega-3 fatty acids, vitamin D or a metabolite thereof, and/or homocysteine in the test sample with one or more reference or control values. The term "reference value" is synonymous with "control value" and broadly includes data that the skilled person would use to facilitate the accurate interpretation of technical data.

Typically, a reference value for each individual biomarker determined in the method is used. The reference value may be a normal level of that biomarker, e.g. a level of the biomarker in the same sample type (e.g. blood, serum or plasma) in a normal subject. The reference value may, for example, be based on a mean or median level of the biomarker in a control population of subjects, e.g. 5, 10, 100, 1000 or more normal subjects (who may either be age- and/or gender-matched or unmatched to the test subject). It is known in the art how to assign correct reference values as they will vary with gender, race, genetic heritage, health status or age, for example.

The reference value may be determined using corresponding methods to the determination of biomarker levels in the test sample, e.g. using one or more samples taken from normal subjects. For instance, in some embodiments biomarker levels in control samples may be determined in parallel assays to the test samples. Alternatively, in some embodiments reference values for the levels of individual biomarkers in a particular sample type (e.g. blood, serum or plasma) may already be available, for instance from published studies. Thus, in some embodiments, the reference value may have been previously determined, or may be calculated or extrapolated, without having to perform a corresponding determination on a control sample with respect to each test sample obtained.

In one embodiment, the omega-3 fatty acid, vitamin D or a metabolite thereof, agent capable of reducing plasma homocysteine levels, or combination of the present disclosure may be administered to a subject who has:
  (a) a level of omega-3 fatty acids less than or equal to a first reference value;
  (b) a level of vitamin D or a metabolite thereof less than or equal to a second reference value; and/or
  (c) a level of homocysteine greater than or equal to a third reference value.

In one embodiment, the method of the invention comprises calculating an index (referred to herein as a Nutritional Risk Index, NRI) comprising the steps:

(a) a level of omega-3 fatty acids is determined and a level of omega-3 fatty acids in the sample from the subject that is less than or equal to a first reference value is assigned a score of n, and a level of omega-3 fatty acids in the sample from the subject that is greater than the first reference value is assigned a score of zero;
  (b) a level of vitamin D or a metabolite thereof is determined and a level of vitamin D or a metabolite thereof in the sample from the subject that is less than or equal to a second reference value is assigned a score of n, and a level of vitamin D or a metabolite thereof in the sample from the subject that is greater than the second reference value is assigned a score of zero; and/or
  (c) a level of homocysteine is determined and a level of homocysteine in the sample from the subject that is greater than or equal to a third reference value is assigned a score of n, and a level of homocysteine in the sample from the subject that is less than the third reference value is assigned a score of zero,
wherein n is a positive integer (e.g. +1), wherein the index is calculated as the sum of scores obtained from steps (a), (b) and/or (c), and wherein a greater index score is indicative of greater pre-disposition (risk) to cognitive decline.

A score of 0 may correspond to a subject improving in cognitive ability when administered the omega-3 fatty acid, vitamin D or a metabolite thereof, agent capable of reducing plasma homocysteine levels, or combination of the present disclosure.

The first, second and/or third reference values may, for example, be determined using clinical laboratory data, for example publically-available data.

In one embodiment, a reference value for erythrocyte EPA and DHA (the first reference value) is about 4.82 weight percent of total fatty acids. A level less than or equal to this first reference value may be assigned a score of n in the index disclosed herein. In one embodiment, a reference value for plasma 25-hydroxyvitamin D is about 20 ng/mL. A level less than or equal to this reference value may be assigned a score of n in the index disclosed herein. In one embodiment, a reference value for plasma homocysteine is about 14 µmol/L. A level greater than or equal to this reference value may be assigned a score of n in the index disclosed herein.

The control or reference values for a biomarker as described herein in a particular sample may be stored in a database and used in order to interpret the results of the method as performed on the subject.

The level of a biomarker in a test sample, for example the level of the omega-3 fatty acids, vitamin D or a metabolite thereof, and/or homocysteine in a sample from the subject, may be compared to the respective level of the same target in one or more cohorts (populations/groups) of control subjects.

The comparison of the level of the omega-3 fatty acids, vitamin D or a metabolite thereof, and/or homocysteine in a sample from the subject may comprise comparing the level to reference values from a population of control subjects that have been divided into quartiles.

In one embodiment, a level of omega-3 fatty acids is determined and a level of omega-3 fatty acids in the sample from the subject that is in the lowest quartile of reference values from a control population is indicative of pre-disposition to cognitive decline.

In one embodiment, a level of vitamin D or a metabolite thereof is determined and a level of vitamin D or a metabolite thereof in the sample from the subject that is in the lowest quartile of reference values from a control population is indicative of pre-disposition to cognitive decline.

In one embodiment, a level of homocysteine is determined and a level of homocysteine in the sample from the subject that is in the highest quartile of reference values from a control population is indicative of pre-disposition to cognitive decline.

In one embodiment, the method of the invention comprises calculating an index (referred to herein as a Nutritional Risk Index, NRI) comprising the steps:

(a) a level of omega-3 fatty acids is determined and a level of omega-3 fatty acids in the sample from the subject that is in the lowest quartile of reference values from a control population is assigned a score of n, and a level of omega-3 fatty acids in the sample from the subject that is outside the lowest quartile is assigned a score of zero;

(b) a level of vitamin D or a metabolite thereof is determined and a level of vitamin D or a metabolite thereof in the sample from the subject that is in the lowest quartile of reference values from a control population is assigned a score of n, and a level of vitamin D or a metabolite thereof in the sample from the subject that is outside the lowest quartile is assigned a score of zero; and/or (c) a level of homocysteine is determined and a level of homocysteine in the sample from the subject that is in the highest quartile of reference values from a control population is assigned a score of n, and a level of homocysteine in the sample from the subject that is outside the highest quartile is assigned a score of zero, wherein n is a positive integer (e.g. +1), wherein the index is calculated as the sum of scores obtained from steps (a), (b) and/or (c), and wherein a greater index score is indicative of greater pre-disposition to cognitive decline.

In one embodiment, a reference value for erythrocyte EPA and DHA is about 4.82 weight percent of total fatty acids. A level lower than this reference value may be assigned a score of n in the index disclosed herein. In one embodiment, a reference value for plasma 25-hydroxyvitamin D is about 15 ng/m L. A level lower than this reference value may be assigned a score of n in the index disclosed herein. In one embodiment, a reference value for plasma homocysteine is about 18.1 μmol/L. A level higher than this reference value may be assigned a score of n in the index disclosed herein.

The reference value for the level of the biomarker as described herein is preferably measured using the same units used to characterise the level of biomarker in the test sample. Thus, if the level of the biomarker as described herein is an absolute value, such as the μmol/L (μM), the reference value may also be based upon the units μmol/L (μM) in individuals in the general population or a selected control population of subjects.

The extent of the difference between the subject's biomarker levels and the corresponding reference values is also useful for determining which subjects would benefit most from certain interventions. The level of the biomarker in the test sample may be increased or decreased by, for example, at least 1%, at least 5%, at least 10%, at least 20%, at least 30%, at least 50% or at least 100% compared to the reference value.

Method of Treatment

The omega-3 fatty acid, vitamin D or a metabolite thereof and/or agent capable of reducing plasma homocysteine levels may be administered simultaneously, sequentially or separately.

The term "combination" or phrases "in combination", "used in combination with" or "combined preparation" as used herein refer to the combined administration of two or more of omega-3 fatty acid, vitamin D or a metabolite thereof and/or agent capable of reducing plasma homocysteine levels simultaneously, sequentially or separately.

The term "simultaneous" as used herein means that the agents are administered concurrently, i.e. at the same time. The term "sequential" as used herein means that the agents are administered one after the other. The term "separate" as used herein means that the agents are administered independently of each other but within a time interval that allows the agents to show a combined, preferably synergistic, effect. Thus, administration "separately" may permit one agent to be administered, for example, within 1 minute, 5 minutes or 10 minutes after the other.

It is to be appreciated that all references herein to treatment include curative, palliative and prophylactic treatment. The treatment of mammals, particularly humans, is preferred. Both human and veterinary treatments are within the scope of the invention.

Dosage

The skilled person can readily determine an appropriate dose of one of the agents of the invention to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. There can of course be individual instances where higher or lower dosage ranges are merited, and such are within the scope of the invention.

Subject

A "subject" (or "individual") refers to either a human or non-human animal. The non-human animal may be a companion animal.

Examples of non-human animals include an avian, bovine, canine, equine, feline, hicrine, lupine, murine, ovine or porcine animal. A "companion animal" is any domesticated animal, and includes, without limitation, cats, dogs, rabbits, guinea pigs, ferrets, hamsters, mice, gerbils, horses, cows, goats, sheep, donkeys, pigs and the like.

In one embodiment, the subject is a human subject. In another embodiment, the subject is a companion animal. Preferably, the subject is a human.

In one embodiment, the subject is an ageing human subject. The term "ageing human subject" may mean a human subject of 50 years of age or more. In one embodiment, the subject is a human subject of at least 50, 55, 60, 65, 70, 75, 80, 85, 90 or 95 years of age. In a preferred embodiment, the subject is a human subject of 50 years of age or more. In a particularly preferred embodiment, the subject is a human subject of 70 years of age or more.

The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals.

For other animals, an "older adult" has exceeded 50% of the average lifespan for its particular species and/or breed within a species. An animal is considered "elderly" if it has surpassed 66% of the average expected lifespan, preferably if it has surpassed the 75% of the average expected lifespan, more preferably if it has surpassed 80% of the average expected lifespan. An elderly cat or dog has an age from birth of at least about 7 years.

Dietary Intervention

The term "dietary intervention" as used herein refers to an external factor applied to a subject which causes a change in the subject's diet.

In one embodiment, the dietary intervention is a diet supplemented with an omega 3 fatty acid. In one embodiment, the dietary intervention is a diet supplemented with vitamin D. In one embodiment, the dietary intervention is a diet supplemented with an agent capable of reducing plasma homocysteine levels.

In one embodiment, the dietary intervention comprises increasing omega-3 fatty acid intake by the subject, preferably by administering an omega 3 fatty acid supplement. In one embodiment, the dietary intervention comprises increasing vitamin D intake by the subject, preferably by administering a vitamin D supplement. In one embodiment, the dietary intervention comprises increasing intake of an agent capable of reducing plasma homocysteine levels by the subject, preferably by administering a supplement of an agent capable of reducing plasma homocysteine levels.

The diet may be one which is adjusted to the starting body weight of the subject.

The dietary intervention may comprise administration of at least one diet product. The diet product may be a meal replacement product or a supplement product. The diet product may include food products, drinks, pet food products, food supplements, nutraceuticals, food additives or nutritional formulae.

Compositions

The agents and compositions of the invention may increase cognitive function in an individual (e.g. a non-demented individual) susceptible to or suffering from a decline in cognitive function, such as that brought about by the ageing process. The agents and compositions of the invention may prevent, reduce or delay a decline in cognitive function in an individual (e.g. a non-demented individual) susceptible to or suffering from a decline in cognitive function, such as that brought about by the ageing process. In some embodiments, the methods of the invention comprise, prior to the administration, identifying the individual as having cognitive aging or being at risk of cognitive aging. For example, the methods can comprise, prior to the administration, identifying the individual as being in need of improved cognitive ability. The agents and compositions of the invention may decrease brain atrophy and neuroinflammation and increase amyloid-β phagocytosis and the number of synapses.

The omega-3 fatty acid, vitamin D or a metabolite thereof and/or agent capable of reducing plasma homocysteine levels (i.e. agents of the invention) may be administered simultaneously, sequentially or separately.

The omega-3 fatty acid, vitamin D or a metabolite thereof and/or agent capable of reducing plasma homocysteine levels may be comprised within one or more compositions.

In one embodiment, the omega 3 fatty acid, vitamin D or a metabolite thereof and/or agent capable of reducing plasma homocysteine levels is in the form of a food product, preferably further comprising an ingredient selected from the group consisting of protein, carbohydrate, fat and combinations thereof.

In one embodiment, the omega 3 fatty acid, vitamin D or a metabolite thereof and/or agent capable of reducing plasma homocysteine levels is in the form of a pharmaceutical composition further comprising a pharmaceutically acceptable carrier, diluent or excipient.

In various embodiments, the omega 3 fatty acid is 1 to 50 wt. % of the food product or composition, preferably 1 to 30 wt. % of the food product or composition, and most preferably 1 to 15 wt. % of the food product or composition. Preferably, the omega 3 fatty acid comprises at least one of eicosapentaenoic acid (EPA) or docosahexaenoic acid (DHA), and more preferably comprises both EPA and DHA. A daily dose of the food product or composition preferably provides 0.5 g to 1.0 g of DHA per day and/or 0.5 g to 1.0 g of EPA per day, more preferably 0.7 g to 1.0 g of DHA per day and/or 0.6 mg to 0.75 g of EPA per day, and most preferably about 770 mg of DHA per day and/or about 700 mg of EPA per day.

In one embodiment, the omega-3 fatty acids are administered at a dosage of 0.5 g to 2.0 g per day, such as 0.5 g to 1.5 g per day. In one embodiment, the subject is administered 0.5 g to 1.0 g of DHA per day and/or 0.5 g to 1.0 g of EPA per day, more preferably 0.7 g to 1.0 g of DHA per day and/or 0.6 mg to 0.75 g of EPA per day, and most preferably about 770 mg of DHA per day and/or about 700 mg of EPA per day.

The omega 3 fatty acid may comprise a blend of one or more sources of omega 3 fatty acids, and each of the one or more sources of omega 3 fatty acids can be natural (e.g. fish oil) or synthetic (i.e. formed through a process manipulated by a human, as opposed to those of natural origin). The term "fish oil" as used herein means a crude or purified fatty or oily extract rich in omega 3 fatty acids and obtained from a sea individual, preferably a cold-water fish such as, but not limited to, salmon, tuna, mackerel, herring, sea bass, striped bass, halibut, catfish and sardines, as well as shark, shrimp and clams, or any combination thereof.

In one embodiment, the food product or composition is administered in a daily dose that provides 60-2000 IU/day of the Vitamin D or metabolite thereof.

In one embodiment, the food product or composition is administered in a daily dose that provides 0.001 mg/day to 0.1 mg/day of the Vitamin D or metabolite thereof, for example 0.01 mg/day to 0.05 mg/day of the Vitamin D or metabolite thereof, preferably about 0.015 mg/day of the Vitamin D or metabolite thereof.

In one embodiment, the Vitamin D or metabolite thereof is administered at a dosage of 60-2000 IU/day.

In one embodiment, the Vitamin D or metabolite thereof is administered at a dosage of 0.001 mg/day to 0.1 mg/day, for example 0.01 mg/day to 0.05 mg/day, preferably about 0.015 mg/day.

In one embodiment, the agent capable of reducing plasma homocysteine levels is vitamin B6 and/or vitamin B9.

In one embodiment, the food product or composition is administered to the individual in a daily dose that provides at least 0.01 to 100 times the recommended daily requirement (RDA) of the Vitamin B6 per day, for example 10 to 80 times the RDA of the Vitamin 36, and/or 0.01 to 5.0 times the RDA of the Vitamin B9 per day, for example 1.0 to 2.5 times the RDA of the Vitamin B9. The RDA of Vitamin B6 is 1.3 mg/day, and thus the food product or composition can be administered in a daily dose that provides 0.13 mg/day to 130 mg/day of the Vitamin B6, for example 13 mg/day to 100 mg/day of the Vitamin B6. The RDA of Vitamin B9 is 0.4 mg/day, and thus the food product or composition can be administered in a daily dose that provides 0.004 mg/day to 2.0 mg/day of the Vitamin B9, for example 0.4 mg/day to 1.0 mg/day of the Vitamin B9. Nevertheless, the present disclosure is not limited to a specific daily dose of the Vitamin B6 or a specific daily dose of the Vitamin B9.

In one embodiment, the subject is administered at least 0.01 to 100 times the RDA of Vitamin B6 per day, for example 10 to 80 times the RDA of Vitamin B6, and/or 0.01 to 5.0 times the RDA of Vitamin B9 per day, for example 1.0 to 2.5 times the RDA of Vitamin B9. In one embodiment, the subject is administered 0.13 mg/day to 130 mg/day of Vitamin B6, for example 13 mg/day to 100 mg/day of Vitamin B6. In one embodiment, the subject is administered 0.004 mg/day to 2.0 mg/day of Vitamin 39, for example 0.4 mg/day to 1.0 mg/day of Vitamin B9.

In one embodiment, the food product or composition can optionally comprise a nitric oxide releasing compound.

In another embodiment, the food product or composition does not comprise a nitric oxide releasing compound.

The nitric oxide releasing compound is any compound or compounds that cause or can result in the release of nitric oxide in an individual. The nitric oxide releasing compound preferably comprises one or more of arginine, citrulline, ornithine or a peptide or protein containing at least one of these amino acids, more preferably arginine and/or citrulline, and even more preferably comprises citrulline, which provides beneficial effects on the cardiovascular system, specifically in terms of improving blood flow, endothelial function and blood pressure. In various embodiments, the nitric oxide releasing compound is 1 to 20 wt. % of the food product or composition, preferably 1 to 15 wt. % of the food product or composition, and more preferably 1 to 10 wt. % of the food product or composition. In one embodiment, a daily dose of the food product or composition provides from 0.5 g to 10.0 g of the nitric oxide releasing compound (e.g., citrulline) per day, preferably 1.0 g to 5.0 g per day, more preferably 2.0 g to 4.0 g per day, and most preferably about 3.0 g per day.

The food product or composition can further comprise at least one B Vitamin additional to the Vitamin B6 and/or the Vitamin B9, for example one or more of Vitamin B1 (thiamine), Vitamin B2 (riboflavin), Vitamin B3 (niacin), Vitamin B5 (pantothenic acid), Vitamin B7 (biotin) and Vitamin B12 (Cobalamin) or salts, conjugates or derivatives thereof that have B vitamin activity. The food product or composition can optionally comprise from 0.1 to 40 times the RDA of one or more of these additional B vitamins, preferably 1 to 20 times the RDA, and more preferably 1 to 10 times the RDA. In an embodiment, the food product or composition further comprises all of Vitamin B1 (thiamine), Vitamin B2 (riboflavin), Vitamin B3 (niacin), Vitamin B5 (pantothenic acid), Vitamin B7 (biotin) and Vitamin B12 (cobalamin).

In one embodiment, the food product or composition comprising a combination of an omega-3 fatty acid, at least 0.01 to 100 times the recommended daily requirement (RDA) of Vitamin B6 per day and/or 0.01 to 5.0 times the RDA of the Vitamin B9 per day, also preferably provides 0.1 to 40 times the recommended daily requirement (RDA) of Vitamin B12 per day, e.g. 1 to 10 times the recommended daily requirement (RDA) of Vitamin B12 per day.

The Vitamin B12 may thus be administered as a further B Vitamin in a daily dose of about 10, 20, 30 or 40 times the RDA of the Vitamin B12 per day. Preferably, the daily dose provides 10 to 40, more preferably 10 to 30 or even more preferably 10 to 25 times the RDA of the Vitamin B12 per day, most preferably about 12 to 21 times the RDA of the Vitamin B12 per day.

In another embodiment, the food product or composition comprising a combination of an omega-3 fatty acid, at least 0.01 to 100 times the recommended daily requirement (RDA) of Vitamin B6 per day and/or 0.01 to 5.0 times the RDA of the Vitamin B9 per day, also preferably provides 50 to 500 times the recommended daily requirement (RDA) of Vitamin B12 per day, e.g. 100 to 300 times the recommended daily requirement (RDA) of Vitamin B12 per day, preferably 150 to 250 times the recommended daily requirement (RDA) of Vitamin B12 per day.

The Vitamin B12 may thus be administered as a further B vitamin in a daily dose of about 50, 100, 150, 200, 250, 300, 350, 400, 450 or 500 times the RDA of the Vitamin B12 per day. Preferably, the daily dose provides 50 to 500, more preferably 100 to 300 or even more preferably 150 to 250 times the RDA of the Vitamin B12 per day.

The United States RDA of Vitamin B12 is 2.4 micrograms daily for humans of age 14 years and older, so such individuals may be administered a daily dose of the food product or composition that provides also about 0.002 mg to about 0.4 mg of Vitamin B12 per day, preferably 0.02 mg to 0.07 mg of Vitamin B12 per day, more preferably 0.03 mg to 0.05 mg of Vitamin B12 per day, or such individuals may be administered a daily dose of the food product or composition that provides also about 0.1 mg to about 1.2 mg of Vitamin B12 per day, preferably 0.2 mg to 0.7 mg of Vitamin B12 per day, more preferably 0.4 mg to 0.6 mg of Vitamin B12 per day.

In a preferred embodiment, the subject is further administered Vitamin B12. In one embodiment, the vitamin B12 is administered at a dosage of 0.1 to 40 times the RDA of vitamin B12 per day, preferably 10 to 40, 10 to 30 or 10 to 25 times the RDA of vitamin B12 per day, more preferably 12 to 21 times the RDA of vitamin B12 per day.

In one embodiment, the vitamin B12 is administered at a dosage of about 0.002 mg to about 0.4 mg per day, preferably 0.02 mg to 0.07 mg per day, more preferably 0.03 mg to 0.05 mg per day.

In one embodiment, the omega-3 fatty acid; vitamin D or a metabolite thereof; and/or agent capable of reducing plasma homocysteine levels are administered to the subject simultaneously, sequentially or separately with vitamin B12, wherein the vitamin B12 is administered at a dosage of 0.1 to 40 times the RDA of vitamin B12 per day, preferably 10 to 40, 10 to 30 or 10 to 25 times the RDA of vitamin B12 per day, more preferably 12 to 21 times the RDA of vitamin B12 per day.

In a preferred embodiment, the subject is further administered Vitamin B12. In one embodiment, the vitamin B12 is administered at a dosage of 50 to 500 times the RDA of vitamin B12 per day, preferably 100 to 300 or 150 to 250 times the RDA of vitamin B12 per day.

In one embodiment, the vitamin B12 is administered at a dosage of about 0.1 mg to about 1.2 mg per day, preferably 0.2 mg to 0.7 mg per day, more preferably 0.4 mg to 0.6 mg per day.

In one embodiment, the omega-3 fatty acid; vitamin D or a metabolite thereof; and/or agent capable of reducing plasma homocysteine levels are administered to the subject simultaneously, sequentially or separately with vitamin B12, wherein the vitamin B12 is administered at a dosage of 50 to 500 times the RDA of vitamin B12 per day, preferably 100 to 300 or 150 to 250 times the RDA of vitamin B12 per day.

In some embodiments, the food product or composition can further comprise one or more antioxidants to protect against oxidative damage and inflammation-induced damage. Non-limiting examples of suitable antioxidants include Vitamin C, Vitamin D, Vitamin E, selenium, and combinations thereof. For example, the food product or composition can comprise 0.0001 wt. % to 25 wt. % of the antioxidant, if present; preferably 0.0001 wt. % to about 15 wt. %; more preferably 0.001 wt. % to 5 wt. %; and most preferably 0.001 wt. % to 2 wt. %.

In one embodiment, the composition is a food composition (food product) for a human and/or a pet such as a companion individual. The food composition may comprise one or more additional substances such as a mineral, another vitamin, a salt, or a functional additive such as flavouring, a colourant, an emulsifier, or an antimicrobial compound or other preservative. Non-limiting examples of suitable minerals include calcium, phosphorous, potassium, sodium, iron, chloride, boron, copper, zinc, magnesium, manganese and iodine. Non-limiting examples of suitable additional vitamins include fat soluble vitamins as A, D, E and K.

In one embodiment, the composition is a pharmaceutical composition comprising one or more pharmaceutically acceptable carriers, diluents or excipients. Generally, pharmaceutical compositions are prepared by admixing the omega-3 fatty acid, vitamin D or a metabolite thereof and/or agent capable of reducing plasma homocysteine levels with one or more of an excipient, a buffer, a binder, a plasticiser, a colourant, a diluent, a compressing agent, a lubricant, a flavourant or a moistening agent.

The omega-3 fatty acid, vitamin D or a metabolite thereof and/or agent capable of reducing plasma homocysteine levels may have an acute effect that can be seen in less than one month. Additionally or alternatively, the omega-3 fatty acid, vitamin D or a metabolite thereof and/or agent capable of reducing plasma homocysteine levels can have a long-term effect, and thus various embodiments comprise administration to the individual (e.g. orally) for a time period of at least one month; preferably at least two months, more preferably at least three, four, five or six months; most preferably for at least one year. During the time period, the omega-3 fatty acid, vitamin D or a metabolite thereof and/or agent capable of reducing plasma homocysteine levels can be administered to the individual at least one day per week; preferably at least two days per week, more preferably at least three, four, five or six days per week; most preferably seven days per week. The omega-3 fatty acid, vitamin D or a metabolite thereof and/or agent capable of reducing plasma homocysteine levels can be administered in a single dose per day or in multiple separate doses per day.

Kit

In another aspect, the invention provides a kit comprising the omega-3 fatty acid, vitamin D or a metabolite thereof and/or agent capable of reducing plasma homocysteine levels of the invention.

The omega-3 fatty acid, vitamin D or a metabolite thereof and/or agent capable of reducing plasma homocysteine levels may be provided in suitable containers.

The kit may also include instructions for use.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art.

EXAMPLES

Example 1

The Multi-domain Alzheimer Preventive Trial (MAPT) was designed to assess the efficacy of an omega 3 supplement (DHA 800 mg, EPA 200 per day), a multi-domain intervention (nutritional counselling, physical exercise, cognitive stimulation) or a combination of the supplement+ multi domain versus a placebo in reducing rate of cognitive decline in adults of 70 years of age or older. Post hoc analysis of MAPT results suggest that omega 3 supplementation prevents cognitive decline in subjects with lower omega 3 status at baseline. The VITACOG trial demonstrated that homocysteine lowering B vitamins can attenuate total brain atrophy in subjects aged 70 and older with MCI and hyperhomocysteinemia. Two subsequent post hoc reports from VITACOG demonstrated that the B vitamin effects were most pronounced on total brain atrophy and cognitive decline in subjects in the highest tertile of baseline omega 3 status. Baseline nutritional status and nutrient interaction are legitimate design elements to consider for future nutritional interventions. These new insights have led to next generation clinical trials targeting subjects at "nutritional risk" (clinicaltrials.gov: NCT01953705) and nutrient combinations that leverage interactive metabolism may prove more capable of preventing cognitive decline. Implementing these clinical trial design elements (e.g., enrichment and or oversampling) first requires a strong scientific rationale for doing so since it adds cost and operational burden to any clinical trial. Using the MAPT trial data, we tested the hypothesis that baseline nutritional status, reflected by plasma homocysteine, serum vitamin D and erythrocyte omega 3 fatty acids are each independent risk factors for cognitive decline, but when combined using a "nutritional risk index" they compound the risk illustrated by acceleration in the rates of cognitive decline over 36 months.

Results

TABLE 1

| | | | | | | Plasma Homocysteine | |
| | | RBC EPA + DHA | | Serum Vitamin D | | (n = 712) | |
| Baseline characteristics of the MAPT participants | | (n = 712) | | | Insufficient | | Insufficient |
| | Total (n = 712) | Sufficient (n = 524) | Insufficient (n = 188) | Sufficient (n 390) | <20 ng/mL (n = 322) | Sufficient (n 292) | ≥14 μmol/L (n = 420) |
| Age, years, mean (SD) [1] | 75.6 (4.5) | 75.5 (4.5) | 76.1 (4.5) | 75.0 (4.2) | 76.3 (4.8) | 74.6 (4.0) | 76.3 (4.7) |
| Women, n (%) | 480 (67.4) | 356 (67.9) | 124 (66.0) | 266 (68.2) | 214 (66.5) | 231 (79.1) | 249 (59.3) |

TABLE 1-continued

Baseline characteristics of the MAPT participants

| | Total (n = 712) | RBC EPA + DHA (n = 712) | | Serum Vitamin D | | Plasma Homocysteine (n = 712) | |
| | | Sufficient (n = 524) | Insufficient (n = 188) | Sufficient (n 390) | Insufficient <20 ng/mL (n = 322) | Sufficient (n² 92) | Insufficient ≥14 μmol/L (n = 420) |
|---|---|---|---|---|---|---|---|
| Education | | | | | | | |
| No diploma/ primary school | 168 (23.6) | 104 (19.9) | 64 (34.0) | 71 (18.2) | 97 (30.1) | 66 (22.6) | 102 (24.3) |
| Secondary education | 244 (34.3) | 184 (35.1) | 60 (31.9) | 148 (37.9) | 96 (29.8) | 98 (33.5) | 146 (34.8) |
| High-school diploma | 104 (14.6) | 82 (15.7) | 22 (11.7) | 52 (13.3) | 52 (16.1) | 48 (16.4) | 56 (13.3) |
| University level | 196 (27.5) | 154 (29.4) | 42 (22.3) | 119 (30.5) | 77 (23.9) | 80 (27.4) | 116 (27.6) |
| MMSE | 28.0 (1.6) | 28.1 (1.6) | 27.8 (1.8) | 28.1 (1.6) | 27.9 (1.7) | 27.9 (1.6) | 28.1 (1.6) |
| Cognitive composite Z | −0.029 (0.70) | 0.015 (0.66) | −0.15 (0.78) | 0.049 (0.66) | −0.12 (0.73) | 0.07 (0.63) | −0.10 (0.74) |
| APOE4 available, N (%) | 624 (87.6) | 472 (90.1) | 152 (80.9) | 346 (88.7) | 278 (86.3) | 261 (89.4) | 363 (86.4) |
| APOE4 carrier, N (%) | 129 (20.7) | 97 (20.6) | 32 (21.1) | 74 (21.4) | 55 (19.8) | 50 (19.2) | 79 (21.8) |
| Treatment Arm | | | | | | | |
| O3 | 180 (25.3) | 126 (24.1) | 54 (28.9) | 96 (24.6) | 84 (26.1) | 67 (22.9) | 113 (26.9) |
| Multi-Domain | 176 (24.7) | 141 (26.9) | 34 (18.2) | 94 (24.1) | 82 (25.5) | 77 (26.4) | 99 (23.6) |
| O3 + Multi-Domain | 177 (24.9) | 126 (24.1) | 51 (27.3) | 100 (25.6) | 77 (23.9) | 71 (24.3) | 106 (25.2) |
| Placebo | 179 (25.1) | 131 (25.0) | 48 (25.7) | 100 (25.6) | 79 (24.5) | 77 (26.4) | 102 (24.3) |
| RBC EPA + DHA wt % | 5.8 (1.5) | 6.4 (1.2) | 4.0 (0.6) | 5.9 (15) | 5.6 (1.4) | 6.2 (1.5) | 5.5 (1.4) |
| Serum vitamin D, ng/mL | 23.7 (12.3) | 24.1 (12.5) | 22.6 (11.7) | 31.7 (10.4) | 13.7 (4.3) | 24.0 (12.9) | 23.5 (11.8) |
| Plasma homocysteine, umol/L | 15.8 (5.3) | 15.3 (5.3) | 17.1 (5.3) | 15.6 (5.0) | 16.0 (5.7) | 11.4 (1.7) | 18.8 (4.9) |

[1] Mean (SD) or Number (% of total)

Table 1. Baseline characteristics of the MAPT analytical sample

Figure 2:
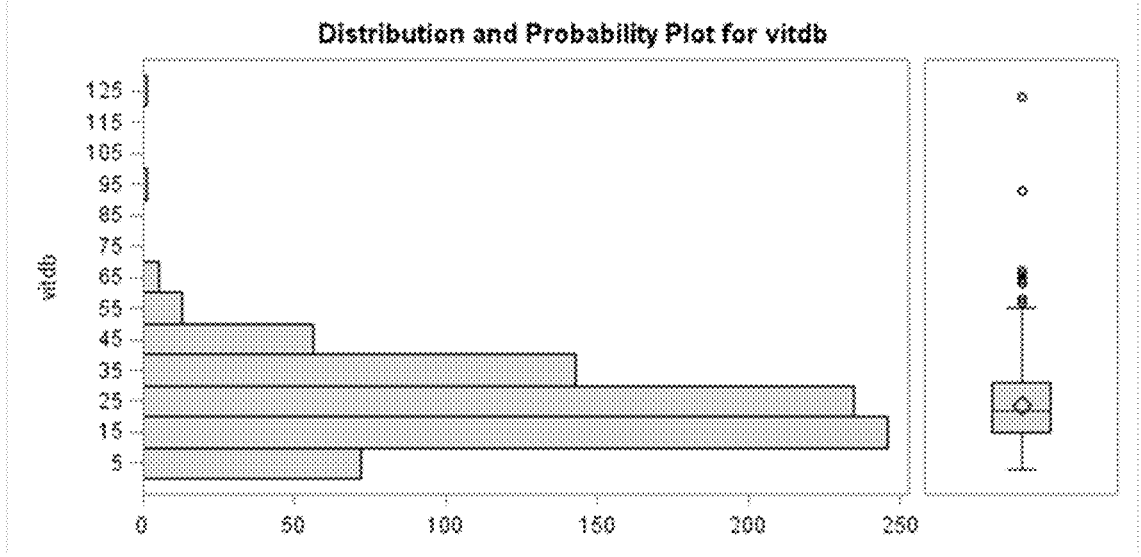
Figure 3:
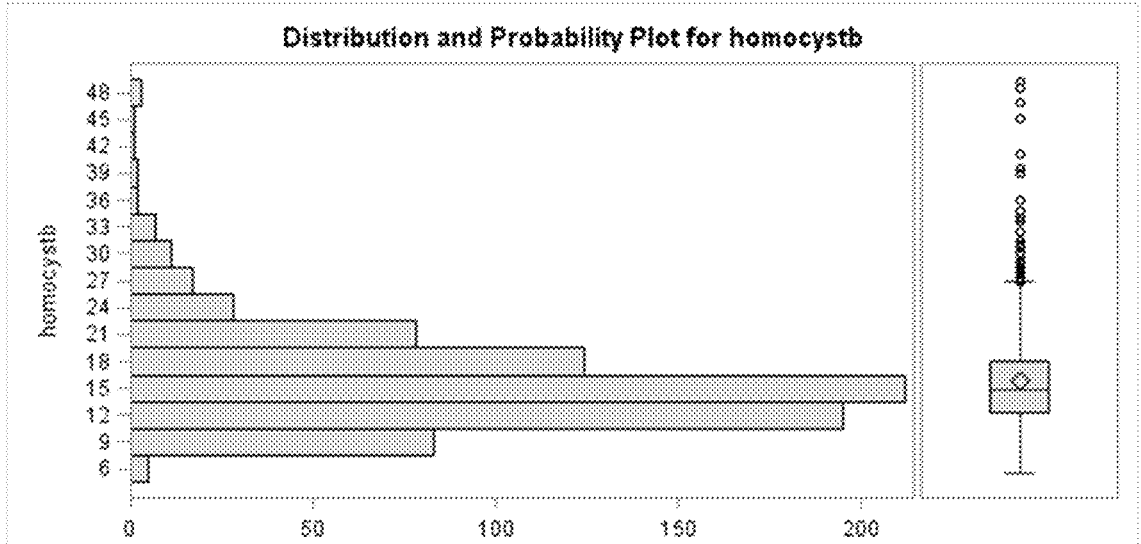

Approximately 25% of the MAPT participants from each treatment arm underwent nutrient biomarker analysis at baseline. This yielded an analytical sample of 712 participants with an average age of 75.6 (4.5), mean MMSE of 28, 67.4% were female and 20.7% were carrying an APOE4 allele (Table 1). The demographic and clinical characteristics were similar to the parent MAPT participants (n=1680) (e.g. mean age 75.3; mean MMSE 28; 64% female; APOE4 carriers 23%). The red blood cell (RBC) EPA+DHA 25th percentile, median and 75th percentile was 4.8, 5.7 and 6.7, respectively. The serum vitamin D 25th percentile, median and 75th percentile was 15, 22, 31 ng/mL, respectively and 12.2, 14.9, 18.1 umol/L for plasma homocysteine (FIGS. 2 and 3).

There were 573 of 712 participants (80.4%) that met criteria for nutritional risk (NRI≥1) and 40.8% (291/712) that carried at least two nutritional risk factors at MAPT entry (NRI≥2). The prevalence of each NRI score ranged from 9.3% (NRI=3, n=66/712) to 19.5% (NRI=0, n=139/712) and yielded 8 possible distinct nutritional risk profiles. The prevalence of insufficient RBC EPA+DHA (≤4.82%), serum vitamin D (≤20 ng/ml), and plasma homocysteine (a 14 umol/L) was 26.4%, 45.2%, and 62.7%, respectively. The prevalence of having two nutritional risk factors (NRI=2) was 31.6%, ranging from 3.8% for insufficient vitamin D and omega 3 combined (NRI-D+O3=2, n=27/712) to 17.6% for vitamin D and homocysteine combined (NRI-D+HCy=2, n=66/712) (Table 2).

TABLE 2

Prevalence of nutritional risk in the MAPT (n = 712)[#]

| Nutritional Risk Index | RBC EPA + DHA Sufficient | Insufficient ≤4.82% | Serum vitamin D Sufficient | Insufficient ≤20 ng/ml | Plasma homocysteine Sufficient | insufficient ≥14 μmol/L | Sample Size n (%) |
|---|---|---|---|---|---|---|---|
| 0 | X | | X | | X | | 139 (19.5) |
| 1 | | X | X | | X | | 22 (3.1) |
| | X | | | X | X | | 104 (14.6) |
| | X | | X | | | X | 156 (21.9) |
| 2 | X | | | X | | X | 125 (17.6) |
| | | X | | X | X | | 27 (3.8) |
| | | X | X | | | X | 73 (10.3) |
| 3 | | X | | X | | X | 66 (9.3) |
| | | 188/712 | | 322/712 | 447/712 | | 712 |

Table 2. Prevalence of nutritional risk in the MAPT.
[#]Shading in the "Insufficient" column indicates insufficient nutritional status. Prevalence of insufficient RBC EPA + DHA is 26.4% (188/712), insufficient serum vitamin D is 45.2% (322/712), insufficient homocysteine is 62.7% (447/712).

TABLE 3

Mean differences in rates of change in the cognitive composite Z score
as a function of the baseline Nutritional Risk Index in the Multi-domain
Alzheimer Prevention Trial (n = 712)[1]
Table 3. Nutritional risk index scores and rates of cognitive decline
over 3-years in adjusted mixed models.

| | β coefficient estimate | SE | Pr > \|t\| |
|---|---|---|---|
| Intercept | 2.4787 | 0.4296 | <.0001 |
| Age, years | −0.03293 | 0.005592 | <.0001 |
| Time, years | 0.01686 | 0.02115 | 0.4256 |
| Men compared to Women | −0.1869 | 0.05320 | 0.0005 |
| Education | | | |
| No diploma/primary school | 0 | — | — |
| Secondary education | 0.1004 | 0.06656 | 0.1317 |
| High-school diploma | 0.4657 | 0.08287 | <0.0001 |
| College or more | 0.4671 | 0.07060 | <0.0001 |
| Nutritional Risk Index, baseline | | | |
| 0 | 0 | — | — |
| 1 | −0.1408 | 0.06862 | 0.0403 |
| 2 | −0.1010 | 0.07222 | 0.1621 |
| 3 | −0.3864 | 0.1004 | 0.0001 |
| Trial arms, baseline | | | |
| Placebo | 0 | — | — |
| Multidomain | −0.04961 | 0.06934 | 0.4745 |
| Omega 3 | −0.03090 | 0.06926 | 0.6555 |
| Omega 3 - multidomain | −0.09266 | 0.06933 | 0.1816 |
| Nutritional Risk Index, longitudinal, years | | | |
| 0 * time (reference group) | 0 | — | — |
| 1 * time | −0.04513 | 0.02117 | 0.0331 |
| 2 * time | −0.08757 | 0.02197 | <.0001 |
| 3 * time | −0.1101 | 0.03274 | 0.0008 |
| Trial arms, longitudinal, years | | | |
| Placebo * time | 0 | — | — |
| Multidomain * time | 0.01654 | 0.02228 | 0.4581 |

TABLE 3-continued

Mean differences in rates of change in the cognitive composite Z score
as a function of the baseline Nutritional Risk Index in the Multi-domain
Alzheimer Prevention Trial (n = 712)[1]
Table 3. Nutritional risk index scores and rates of cognitive decline
over 3-years in adjusted mixed models.

| | β coefficient estimate | SE | Pr > \|t\| |
|---|---|---|---|
| Omega 3 * time | 0.01757 | 0.02225 | 0.4299 |
| Omega 3 + MD * time | 0.04795 | 0.02234 | 0.0320 |

[1]Nutritional risk index increases by one point for any of the following evidence-based criteria: RBC EPA + DHA ≤ 4.82 wt. % of total; Serum 25-hydroxyvitamin D ≤ 20 ng/mL; plasma homocysteine ≥ 14 umol/L; Model adjusted for baseline age, [time], gender, education, trial arm. Trial arm baseline and time effects not shown; Solution for the fixed effects using the cognitive composite Z score as the outcome measure The overall rate of annual change in the cognitive composite Z score was −0.008 standard units (SU) (0.024 SU over the 3 years follow up period). In the mixed-effects models adjusted for age, gender, education, and trial arms, each NRI point increase was associated with an incremental increase in the mean rate of cognitive decline (FIG. 1A). These estimated effects indicate that those elders without nutritional risk index (NRI=0) exhibited a cumulative improvement in cognitive performance by an average of 0.09 SU on the cognitive composite Z score over the 3-year trial period. By comparison, those entering the trial with the maximum nutritional risk (NRI=3) experienced on average a 0.33 SU decline on the cognitive composite Z score over the 3-year trial period. This difference in the estimated effect size between NRI=0 versus 3 on rates of change in cognitive function is equivalent to being 13.75 years younger in age (Table 3). We also adjusted for CDR (0 vs. 0.5) and its interaction with time, APOE4 carrier status and its interaction with time, and "education" time interactions, and the coefficients for each NRI were essentially unchanged (data not shown). Restricting the analysis to participants naïve to the omega 3 supplementation again yielded consistent results: 1) placebo group only (n=179) NRI=1, 0=−0.100, p=0.021; NRI=2, 6=−0.108, p=0.01; NRI=3, β=−0.202, p=0.005, (Table 1) and 2) placebo and multidomain arms only (n=355) NRI=1, β=−0.082, p=0.006; NRI=2, β=−0.095, p=0.002; NRI=3, 6=−0.195, p=0.0004 (Table 2). The sensitivity analysis of NRI effects on change in cognitive function using population-based quartile thresholds for each nutritional biomarker also produced no material changes in the results (Table 7).

TABLE 4

Mean differences in rates of change in the cognitive composite Z score as a function of each distinct
nutritional risk profile identified at baseline with the Nutritional Risk Index (n = 712)[1]

| | Plasma Homocysteine | Serum 25-OH-D | RBC EPA + DHA | B | SE | p-value |
|---|---|---|---|---|---|---|
| Nutritional Risk Index, Baseline | | | | | | |
| 0 | 0 | 0 | 0 | 0 | — | — |
| 1 | 1 | 0 | 0 | −0.1207 | 0.07739 | 0.119 |
| | 0 | 1 | 0 | −0.1839 | 0.08562 | 0.0318 |
| | 0 | 0 | 1 | −0.04927 | 0.1507 | 0.7437 |
| 2 | 1 | 1 | 0 | −0.112 | 0.08323 | 0.1785 |
| | 1 | 0 | 1 | −0.09128 | 0.09535 | 0.3386 |
| | 0 | 0 | 1 | −0.1493 | 0.1387 | 0.2819 |
| 3 | 1 | 1 | 1 | −0.377 | 0.1009 | 0.0002 |

TABLE 4-continued

Mean differences in rates of change in the cognitive composite Z score as a function of each distinct
nutritional risk profile identified at baseline with the Nutritional Risk Index (n = 712)[1]

| | Plasma Homocysteine | Serum 25-OH-D | RBC EPA + DHA | B | SE | p-value |
|---|---|---|---|---|---|---|
| Nutritional Risk Index Longitudinal, years | | | | | | |
| 0 * time | 0 | 0 | 0 | 0 | — | — |
| 1 * time | 1 | 0 | 0 | −0.03562 | 0.02394 | 0.1369 |
| | 0 | 1 | 0 | −0.06189 | 0.02642 | 0.0193 |
| | 0 | 0 | 1 | −0.02558 | 0.05185 | 0.6218 |
| 2 * time | 1 | 1 | 0 | −0.09778 | 0.02544 | 0.0001 |
| | 1 | 0 | 1 | −0.06944 | 0.03018 | 0.0215 |
| | 0 | 1 | 1 | −0.08783 | 0.04459 | 0.049 |
| 3 * time | 1 | 1 | 1 | −0.1024 | 0.03265 | 0.0017 |

[1]Nutritional risk index increases by a point tor any of the following criteria: RBC EPA + DHA ≤4.82 wt. % of total; Serum 25-hydroxyvitamin D ≤20 ng/mL; plasma homocysteine ≥14; Model adjusted for age, gender, education and trial arm; Solution for the fixed effects using the cognitive composite Z score as the outcome measure
Table 4. Distinct nutritional risk index scores and rates of change in cognitive function over 3-years.

It is possible that the estimated effect of the NRI score on rates of change in cognitive function is not solely dependent on each point increase, but rather the nutritional biomarker and distinct combinations that constitute the NRI score itself. Accordingly, in the same adjusted models we examined the mean rates of change as a function of each of the 8 possible nutritional risk profiles inherent to the NRI (FIG. 1B). Compared with those without nutritional risk (NRI=0), only insufficient serum vitamin D (NRI-D=1) had more rapid rates of cognitive decline (−0.06 SU/year), whereas insufficient RBC EPA+DHA (NRI-O3=1) or plasma homocysteine (NRI-HCy=1) did not (Table 4). However, participants with two nutritional risk factors (NRI=2), regardless of which of the two contributed, an acceleration in rate of cognitive decline was observed ranging from β=−0.06 to −0.09/year (NRI-HCy+O3=2 and NRI-HCy+D=2), respectively (Table 4).

Conclusions

In these adults, age 70 and older with subjective memory concerns we deployed a quantitative and objective nutritional risk index of omega 3 fatty acids, vitamin D and homocysteine to determine the nutrition-related risk for cognitive decline. Insufficient nutritional status was identified in 80.4% of the population with over 40% carrying at least 2 nutritional risk factors. The NRI explained the heterogeneity observed in rates of cognitive decline over 3-years, where each point increase was associated with more rapid rates of cognitive decline. Participants with sufficient nutritional status exhibited a significant learning effect or cognitive enhancement over the trial duration suggesting that optimising concentrations of omega 3 polyunsaturated fatty acids, EPA and DHA, vitamin D and homocysteine can prevent cognitive decline.

To our knowledge, combining omega-3 fatty acids, vitamin D and homocysteine lowering B vitamins to reach optimium nutritional status (RBC EPA+DHA>4.82%, serum vitamin D>20 ng/ml and plasma homocysteine<14 umol/L) has not been formally tested in a clinical trial.

The cut offs for each nutritional biomarker were established a priori using an evidence base where current recommendations for distinct nutritional requirements or sufficient nutrient status for prevention of cognitive decline does not exist. This compelled us to test our criteria using also a "population-based" approach for sake of testing the sensi-tivity of our findings with the initial thresholds and also to inform this area of research in general where recommendations are sorely needed in clinical practice. Although RBC EPA+DHA was already set at the lowest quartile (5 4.82 wt. % qualifies as nutritional risk), the vitamin D was then lower (≤15 versus ≤20 ng/mL) and homocysteine was higher (≥18.1 versus≥14 umol/L) using the distributions observed in the MAPT (Table 6). We were encouraged by the fact that the significant effect estimates were essentially unchanged with the exception of NRI of 3, which arguably had more profound effects on rates of cognitive decline (−0.18/year versus −0.10/year) (Table 7). This also can be interpreted as a "dose effect" where the corresponding impact on rates of cognitive decline are even more pronounced when moving the nutritional risk criteria to more extreme insufficient levels. We included all the data available and adjusted for trial arms in our statistical analysis initially since the between group differences were not apparent in the MAPT combined with a mean rate of cognitive decline of −0.008/year and the historically small effect size of nutrition, albeit using subjective measures (i.e. diet history questionnaires). After the primary analysis including all trial arms was completed we conducted a post-hoc analysis restricted to the omega 3 supplementation naïve only groups to assure the validity of our approach and the sensitivity of the results. This sensitivity analysis in the placebo only group (n=179) generated essentially the same findings with the exception NRI of 1 and 2 producing similar effect estimates on cognitive decline (13=−0.100/year versus −0.108/year) and NRI of 3 almost doubled in magnitude (13=−0.202/year versus −0.110/year) (Table 9). Then were we added the placebo and MD+ placebo groups together and the same theme was apparent (n=355)(NRI=1:13=−0.082/year; NRI=2: 13=−0.095/year; NRI=3: 13=−0.195/year). These internal consistencies are encouraging and support the robustness of the NRI effects on rates of change in cognitive function.

The distribution of the nutritional biomarker concentrations in the MAPT participants are similar to other populations with some exceptions. The mean plasma homocysteine was 15 μmol/L, which is similar to the pre-fortification era in the US and with other countries not undergoing fortification in Europe (Ganguly P et al. (2015) Nutr J 14: 6). However, hyperhomocysteinema was associated with more rapid rates of cognitive decline only when accompanied by another nutritional risk factor using the 14 μmol/L thresholds. These findings are somewhat consistent with other studies, including the VITACOG trial where homocysteine lowering B vitamin supplementation slowed cognitive decline in people with hyperhomocysteinemia and higher omega 3 fatty acids at baseline. It is also worth noting that our analysis compared people with what we describe as optimum of sufficient cognitive nutrition to others with varying nutritional risk. Our inability to detect plasma HCy as an independent nutritional risk factor (and omega 3 for that matter) is likely due to this approach and a distinct difference in other studies more focused on isolated nutrients or related factors. Vitamin D levels were similar to other studies in France, Europe and the US for 70 and older (Feart C et al. (2017) Alzheimers Dement 13: 1207-1216; Goodwill A M et al. (2017) J Am GeriatrSoc 65: 2161-2168), RBC EPA+DHA mean and median were similar to what was seen in the Framingham and the Cardiovascular Health Study, but methodological differences in the assays and tissues examined remain a limitation (Stark K D et al. (2016) Prog Lipid Res 63: 132-152; Heude B et al. (2003) Am J Clin Nutr 77: 803-808).

TABLE 5

Baseline characteristics of the MAPT participants using population-based nutritional biomarker criteria.

| | | RBC Omega 3* (n-712) | | Serum Vitamin D (n-712) | | Plasma Homocysteine (n-712) | |
| | | | Low | | Low | | High |
| | Total (n-712) | High (n-524) | ≤4.82 wt. % (n = 188) | High (n-517) | ≤15 ng/mL (n-195) | Low (n-536) | ≥18.1 μmol/L (n = 176) |
|---|---|---|---|---|---|---|---|
| Age, years, mean (SD)[1] | 75.6 (4.5) | 75.5 (4.5) | 76.1 (4.5) | 75.2 (4.4) | 76.8 (4.8) | 75.3 (4.4) | 76.7 (4.6) |
| Women, n (%) | 480 (67.4) | 356 (67.9) | 124 (66.0) | 355 (68.7) | 125 (64.1) | 381 (71.1) | 99 (56.2) |
| Education | | | | | | | |
| No diploma/ primary school | 168 (23.6) | 104 (19.9) | 64 (34.0) | 111 (21.5) | 57 (29.2) | 130 (24.3) | 38 (21.6) |
| Secondary education | 244 (34.3) | 184 (35.1) | 60 (31.9) | 183 (35.4) | 61 (31.3) | 172 (32.1) | 72 (40.9) |
| High-school diploma | 104 (14.6) | 82 (15.7) | 22 (11.7) | 73 (14.1) | 31 (15.9) | 84 (15.7) | 20 (11.4) |
| University level | 196 (27.5) | 154 (29.4) | 42 (22.3) | 150 (29.0) | 46 (23.6) | 150 (28.0) | 46 (26.1) |
| MMSE | 28.0 (1.6) | 28.1 (1.6) | 27.8 (1.8) | 28.1 (1.6) | 27.8 (1.7) | 28.0 (1.7) | 28.1 (1.5) |
| Cognitive composite Z | −0.029 (0.70) | 0.015 (0.66) | −0.15 (0.78) | 0.012 (0.69) | −0.14 (0.70) | −0.0034 (0.68) | −0.11 (0.74) |
| APOE4 available, N (%) | 624 (87.6) | 472 (90.1) | 152 (80.9) | 457 (88.4) | 167 (85.6) | 477 (89.0) | 147 (83.5) |
| APOE4 carrier, N (%) | 129 (20.7) | 97 (20.6) | 32 (21.1) | 95 (20.8) | 34 (20.4) | 93 (19.5) | 36 (24.5) |
| Treatment Arm | | | | | | | |
| O3 | 180 (25.3) | 126 (24.1) | 54 (28.9) | 136 (26.3) | 44 (22.6) | 130 (24.3) | 50 (28.4) |
| Multi-Domain | 176 (24.7) | 141 (26.9) | 34 (18.2) | 124 (24.0) | 52 (26.7) | 124 (23.1) | 52 (29.6) |
| O3 + Multi-Domain | 177 (24.9) | 126 (24.1) | 51 (27.3) | 132 (25.5) | 45 (23.1) | 137 (25.6) | 40 (22.7) |
| Placebo | 179 (25.1) | 131 (25.0) | 48 (25.7) | 125 (24.2) | 54 (27.7) | 145 (27.1) | 34 (19.3) |
| RBC EPA + DHA | 5.8 (1.5) | 6.4 (1.2) | 4.0 (0.6) | 5.9 (1.5) | 5.5 (1.3) | 5.9 (1.5) | 5.5 (1.3) |
| Serum 25-OH-D | 23.7 (12.3) | 24.1 (12.5) | 22.6 (11.7) | 28.6 (10.9) | 10.8 (3.0) | 23.8 (12.2) | 23.4 (12.6) |
| Plasma homocysteine | 15.8 (5.3) | 15.3 (5.3) | 17.1 (5.3) | 15.5 (5.0) | 16.4 (6.1) | 13.4 (2.7) | 22.9 (5.2) |

*Eicosapentaenoic acid + docosahexaenoic acid quantified as a weight percentage of total 1 Mean (SD) or Number (% of total)

TABLE 6

Prevalence of nutritional risk in the MAPT using population-based criteria (n = 712).

| Nutritional risk index score | RBC EPA + DHA Sufficient | RBC EPA + DHA Insufficient ≤4.82 % | Serum vitamin D Sufficient | Serum vitamin D Insufficient ≤15 ng/ml | Plasma homocysteine Sufficient | Plasma homocysteine Insufficient ≥18.1 μmol/L | Sample size n (%) |
|---|---|---|---|---|---|---|---|
| 0 | X |  | X |  | X |  | 301 (42.3) |
| 1 |  | X | X |  | X |  | 91 (12.8) |
|  | X |  |  | X | X |  | 101 (14.2) |
|  | X |  | X |  |  | X | 85 (12.0) |
| 2 | X |  |  | X |  | X | 37 (5.2) |
|  |  | X |  | X | X |  | 43 (6.0) |
|  |  | X | X |  |  | X | 40 (5.6) |
| 3 |  | X |  | X |  | X | 14 (2.0) |

Shading in the "Insufficient" column indicates nutritional risk based upon population quartiles.

The total prevalence of insufficient RBC EPA+DHA in the analytic sample was 26.4% (188/712). The total prevalence of deficient serum 25-OH-D was 45.2% (322/712) and the prevalence of hyperhomocysteinemia was 62.7% (447/712).

TABLE 7

Sensitivity analysis: Mean differences in rates of change in the cognitive composite Z score as a function of the Nutritional Risk Index using population-based criteria (n = 712).

|  | Estimate | SE | Pr > \|t\| |
|---|---|---|---|
| Intercept | 2.3663 | 0.4269 | <.0001 |
| Age at baseline, years | −0.03337 | 0.005585 | <.0001 |
| Time, years | 0.01127 | 0.01193 | 0.3451 |
| Men compared to Women | −0.1979 | 0.05310 | 0.0002 |
| No diploma/primary school (reference) | 0 | • | • |
| Secondary education | 0.1363 | 0.06646 | 0.0404 |
| High-school diploma | 0.4833 | 0.08281 | <.0001 |
| College or more | 0.5041 | 0.07059 | <.0001 |

TABLE 7-continued

Sensitivity analysis: Mean differences in rates of change in the cognitive composite Z score as a function of the Nutritional Risk Index using population-based criteria (n = 712).

|  | Estimate | SE | Pr > \|t\| |
|---|---|---|---|
| Baseline association Nutritional risk index |  |  |  |
| 0 (reference) | 0 | • | • |
| 1 | −0.01862 | 0.05522 | 0.7360 |
| 2 | −0.2128 | 0.07208 | 0.0032 |
| 3 | 0.01502 | 0.1829 | 0.9346 |
| Longitudinal association Nutritional risk index * time (years) |  |  |  |
| 0 * time (reference) | 0 | • |  |
| 1 * time | −0.04030 | 0.01733 | 0.0202 |
| 2 * time | −0.06156 | 0.02354 | 0.0090 |
| 3 * time | −0.1874 | 0.06791 | 0.0059 |

[1]Nutritional risk index increases by a point for any of the following criteria: RBC EPA: DHA ≤ 4.82 wt. % of total; Serum 25-hydroxyvitamin D ≤ 15 ng/mL; plasma homocysteine ≥ 18.1; Solution for the fixed effects using the cognitive composite Z score as the outcome measure

TABLE 8

Sensitivity analysis: Mean differences in rates of change in the cognitive composite Z score as a function of each distinct nutritional risk profile identified with the Nutritional Risk Index using population-based criteria.

| | Plasma HCy High = 1 ≥18.1 μmol/L | Serum 25-OH-D Low = 1 ≤15 ng/ml | RBC EPA + DHA Low = 1 ≤4.82% | Estimate | SE | Pr > \|t\| |
|---|---|---|---|---|---|---|
| Baseline association Nutritional biomarker combinations |  |  |  |  |  |  |
| Homo*vitd*omega3 (reference) | 0 | 0 | 0 | 0 | • | • |
| Homo*vitd*omega3 | 1 | 0 | 0 | 0.03489 | 0.08176 | 0.6696 |
| Homo*vitd*omega3 | 0 | 1 | 0 | −0.06980 | 0.07576 | 0.3570 |
| Homo*vitd *omega3 | 0 | 0 | 1 | −0.00643 | 0.07924 | 0.9354 |
| Homo*vitd*omega3 | 1 | 1 | 0 | −0.1413 | 0.1172 | 0.2281 |
| Homo*vitd*omega3 | 1 | 0 | 1 | −0.2887 | 0.1110 | 0.0094 |

TABLE 8-continued

Sensitivity analysis: Mean differences in rates of change in the cognitive composite
Z score as a function of each distinct nutritional risk profile identified with the Nutritional Risk
Index using population-based criteria.

|  | Plasma HCy High = 1 ≥18.1 μmol/L | Serum 25-OH-D Low = 1 ≤15 ng/ml | RBC EPA + DHA Low = 1 ≤4.82% | Estimate | SE | Pr > \|t\| |
|---|---|---|---|---|---|---|
| Homo*vitd*omega3 | 0 | 1 | 1 | −0.1968 | 0.1079 | 0.0682 |
| Homo*vitd*omega3 | 1 | 1 | 1 | 0.01773 | 0.1832 | 0.9229 |
| Longitudinal association Nutritional biomarker combination * time (years) | | | | | | |
| Homo*vitd*omega3 (reference) | 0 | 0 | 0 | 0 | • | |
| Homo*vitd*omega3 | 1 | 0 | 0 | −0.04541 | 0.02606 | 0.0817 |
| Homo*vitd*omega3 | 0 | 1 | 0 | −0.04034 | 0.02356 | 0.0870 |
| Homo*vitd*omega3 | 0 | 0 | 1 | −0.03568 | 0.02546 | 0.1613 |
| Homo*vitd*omega3 | 1 | 1 | 0 | −0.07196 | 0.03801 | 0.0585 |
| Homo*vitd*omega3 | 1 | 0 | 1 | −0.03978 | 0.03867 | 0.3038 |
| Homo*vitd*omega3 | 0 | 1 | 1 | −0.07059 | 0.03539 | 0.0463 |
| Homo*vitd*omega3 | | 1 | 1 | −0.1876 | 0.06815 | 0.0060 | age, time, sex, and education were controlled in the model

25

TABLE 9

Sensitivity analysis: Mean differences in rates of change in the cognitive composite
Z score as a function of the Nutritional Risk Index restricted to the placebo
group only (n = 179).

| Effect | groupe trt Mapt 4cl | edu | index2014 | Estimate | Standard Error | DF | t Value | Pr > \|t\| |
|---|---|---|---|---|---|---|---|---|
| Intercept | | | | 2.0207 | 0.7793 | 170 | 2.59 | 0.0103 |
| age | | | | −0.02753 | 0.01007 | 428 | −2.74 | 0.0065 |
| year | | | | 0.04213 | 0.03317 | 160 | 1.27 | 0.2059 |
| sexe | | | | −0.1909 | 0.09960 | 428 | −1.92 | 0.0560 |
| edu | | 1 | | 0.1077 | 0.1309 | 428 | 0.82 | 0.4109 |
| edu | | 2 | | 0.3480 | 0.1451 | 428 | 2.40 | 0.0169 |
| edu | | 3 | | 0.3128 | 0.1395 | 428 | 2.24 | 0.0254 |
| edu | | 0 | | 0 | • | • | • | • |
| index2014 | | | 1 | 0.01589 | 0.1236 | 428 | 0.13 | 0.8978 |
| index2014 | | | 2 | 0.07569 | 0.1256 | 428 | 0.60 | 0.5471 |
| index2014 | | | 3 | −0.3634 | 0.1813 | 428 | −2.00 | 0.0456 |
| index2014 | | | 0 | 0 | • | • | • | • |
| year*index2014 | | | 1 | −0.1004 | 0.04350 | 428 | −2.31 | 0.0214 |
| year*index2014 | | | 2 | −0.1088 | 0.04460 | 428 | −2.44 | 0.0151 |
| year*index2014 | | | 3 | −0.2025 | 0.07195 | 428 | −2.82 | 0.0051 |
| year*index201 4 | | | 0 | 0 | • | • | • | • |
| gpeMapt4c | 4:ctrl | | | 0 | • | • | • | • |
| year*gpeMapt4c | 4:ctrl | | | 0 | • | • | • | • |

TABLE 10

Sensitivity analysis: Mean differences in rates of change in the cognitive
composite Z score as a function of the Nutritional Risk Index restricted to
the placebo and multidomain groups only (n = 355).

| Effect | groupe trt Mapt 4cl | edu | index2014 | Estimate | Standard Error | DF | t Value | Pr > \|t\| |
|---|---|---|---|---|---|---|---|---|
| Intercept | | | | 1.8989 | 0.6151 | 345 | 3.09 | 0.0022 |
| age | | | | −0.02524 | 0.007980 | 845 | −3.16 | 0.0016 |
| year | | | | 0.03437 | 0.02609 | 322 | 1.32 | 0.1886 |
| sexe | | | | −0.1970 | 0.07662 | 845 | −2.57 | 0.0103 |
| edu | | 1 | | 0.1012 | 0.09770 | 845 | 1.04 | 0.3008 |
| edu | | 2 | | 0.3817 | 0.1159 | 845 | 3.29 | 0.0010 |

TABLE 10-continued

Sensitivity analysis: Mean differences in rates of change in the cognitive composite Z score as a function of the Nutritional Risk Index restricted to the placebo and multidomain groups only (n = 355).

| Effect | groupe trt Mapt 4cl | edu | index2014 | Estimate | Standard Error | DF | t Value | Pr > \|t\| |
|---|---|---|---|---|---|---|---|---|
| edu | | 3 | | 0.5031 | 0.1017 | 845 | 4.95 | <.0001 |
| edu | | 0 | | 0 | • | • | • | • |
| index2014 | | | 1 | −0.1587 | 0.09402 | 845 | −1.69 | 0.0918 |
| index2014 | | | 2 | −0.05202 | 0.09787 | 845 | −0.53 | 0.5952 |
| index2014 | | | 3 | −0.4015 | 0.1505 | 845 | −2.67 | 0.0078 |
| index2014 | | | 0 | 0 | • | • | • | • |
| year*index2014 | | | 1 | −0.08231 | 0.0304t | 845 | −2.71 | 0.0069 |
| year*index2014 | | | 2 | −0:09510 | 0.0313.6 | 845 | −3.03 | 0.0025 |
| year*index2014 | | | 3 | −0.1957 | 0.05490 | 845 | −3.56 | 0.0004 |
| year*index2014 | | | 0 | 0 | • | • | • | • |
| gpeMapt4c | 3:IM | | | −0.05348 | 0.06961 | 845 | −0.77 | 0.4425 |
| gpeMapt4c | 4:ctrl | | | 0 | • | • | • | • |
| year*gpeMapt4c | 3:IM | | | 0.01622 | 0.02342 | 845 | 0.69 | 0.4886 |
| year*gpeMapt4c | 4:ctrl | | | 0 | • | • | • | • |

Materials and Methods

Study Population

Briefly, the Multi-domain Alzheimer Prevention Trial (MAPT) (Andrieu S et al. (2017) Lancet Neurol 16: 377-389; Vellas B et al. (2014) J Prev Alzheimers Dis 1: 13-22) was a 3-year, multi-center, randomised, placebo-controlled trial with four parallel groups testing three actives arms, including a multi-domain (MD) intervention plus placebo, supplementation with long chain omega 3 polyunsaturated fatty acids (PUFA), and MD plus omega 3 versus a placebo only group. The trial was conducted at 13 memory centers across France and Monaco by experts in the diagnosis and management of cognitive impairment and dementia. Community dwelling elders age 70 and older met at least one of three criteria: spontaneous memory complaint expressed to their physician, limitation in one instrumental activity of daily living, or gait speed recorded 5 0.8 m/s or >5 s to walk 4 meters. Participants with a Mini Mental State Examination (MMSE) score lower than 24, those in whom dementia was diagnosed, and those with any difficulty in basic activities of daily living were excluded, as were those taking omega 3 PUFA supplements at baseline (Andrieu S et al. (2017) Lancet Neurol 16: 377-389). Blood draw was offered to all the MAPT participants of which 831 volunteered and these samples were banked accordingly. Approximately 25% of the total population from each arm underwent nutrient biomarker analysis (n=791) of which 712 participants had complete data to carry out the primary analysis. The trial protocol was approved by the French Ethics Committee located in Toulouse (CPP SOOM II) and was authorised by the French Health Authority. The current study protocol was approved by the MAPT/DSA that permitted availability of tissue and existing data to carry out the specific research aims.

Neuropsychological Assessments

The primary outcome measures in the MAPT was a cognitive composite Z score constructed from four tasks, including 1) free and total recall of the Free and Cued Selective Reminding Test (Grober E et al. (1988) Neurology 38: 900-903), 2) ten MMSE orientation items, 3) the Digit Symbol Substitution Test score from the Wechsler Adult Intelligence Scale—Revised (Wechsler D. Wechsler adult intelligence scale—revised. New York: Psychological Corp;

1981), and 4) the Category Naming Test [i.e. 2 min category fluency in animals]) (Cardebat D et al. (1990) Acta Neurol Belg 90: 207-217).

Nutritional Biomarker Assays

Erythrocyte membrane omega 3 fatty acids. The percentage concentration of red blood cell membrane eicosapentaenoic acid (EPA, 20:5n-3) and docosahexaenoic acid (DHA, 22:6n-3) was quantified using gas chromatography coupled with a flame ionisation detector. Briefly, erythrocytes are separated from plasma by centrifugation and washed three times before lipid extraction by the Folch method including a mixture of hexane and isopropanol after acidification. Margaric acid (Sigma) is added as an internal standard. Total lipid extracts were saponified and methylated. Fatty acid methyl esters were extracted with pentane and analysed by gas chromatography (GC) using an Agilent Technologies 6890N gas chromatograph with a split injector, a bonded silica capillary column (BPX 70, 60 m×0.25 mm; 0.25 µm film thickness) and a flame ionisation detector. Helium was used as a carrier gas, the column temperature program started at 150° C., increased by 1.3° C./min to 220° C. and held at 220° C. for 10 min (Legrand P et al. (2010) Lipids 45: 11-19). Identification of FAME was based on retention times obtained for FAME prepared from fatty acid standards. The area under the curve was determined using ChemStation software (Agilent). EPA and DHA concentrations are calculated using the internal standards and expressed as µg/g of red blood cells. FA methyl esters (FAME) are quantifiable after trans methylation using FAME analysis using a GC 2100 Gas Chromatograph (Shimadzu) equipped with a CP Wax 58CB 50-m fused silica capillary column. Programmed temperature spray injector and a flame ionisation detector calculate the EPA and DHA and expressed as % of total fatty acids as labeled as RBC EPA+DHA.

Serum 25-hydroxyvitamin D. An electrochemiluminescence binding assay was utilised for the in-vitro determination of total 25-hydroxyvitamin D (Cobas 8000, Roche). This assay employs vitamin D binding protein (VDBP) to capture both 25-hydroxyvitamin D3 and D2 with the intention to quantify total serum vitamin D (25-OH) (Holick M F et al. (2009) Ann Epidemiol 19: 73-78). Briefly, the sample is incubated with a pretreatment reagent for 9 minutes denaturing the natural VDBP in the sample to release the bound vitamin D (25-OH-D). The sample is then further incubated with a recombinant ruthenium-labeled VDBP to form a complex of 25-OH-D and the ruthenylated-VDBP. The addition of a biotinylated 25-OH-D creates a complex consisting of the ruthenium-labelled VDBP and the biotinylated 25-0H-D. The entire complex becomes bound to the solid phase by the interaction of biotin and streptavidin-coated microparticles, which are captured on the surface of the electrode. The unbound substances are removed. Adding voltage to the electrode induces chemiluminescent emission which is measured by a photomultiplier. Results are determined via an instrument-specific calibration curve which is generated by 2-point calibration and a calibration master curve provided via the reagent barcode. Units are expressed as ng/mL.

Plasma homocysteine. Total plasma homocysteine was measured using a commercially available enzymatic cycling assay (Cobas 8000, Roche) (Dou C et al. (2005) Clin Chem 51: 1987-1989). The concentration of total plasma homocysteine was measured in μmol/L in plasma samples against a standard curve. Oxidised homocysteine was first reduced and then reacted with S-adenosylmethionine to form methionine and S-adenosyl homocysteine (SAH) in the presence of homocysteine S-methyl transferase. SAH is then assessed by coupled enzyme reactions where SAH is hydrolysed into adenosine and homocysteine by SAH hydrolase and homocysteine is cycled back into the homocysteine conversion reaction, which serves to amplify the detection signal. The formed adenosine is hydrolysed into inosine and ammonia. Glutamate dehydrogenase catalyses the reaction of ammonia with 2-oxoglutarate and NADH to form NAD+. The concentration of homocysteine in the sample is directly proportional to the amount of NADH converted to NAD+, which was read at an absorbance of 340 nm. Units are expressed as μmol/L.

Development of the Nutritional Risk Index of Cognition Using Nutritional Biomarkers The nutritional risk index was conceptualised using the following criteria: 1) quantitative and objective measure of nutrition and metabolism, 2) well validated bioanalytical approaches, 3) include nutritional biomarkers that have biological plausibility in cognitive decline and dementia, and 4) are modifiable through dietary intake or supplementation. Among the nutritional biomarkers meeting these criteria, three were selected: 1) red blood cell membrane eicosapentaenoic acid (20:5n-3) and docosahexaenoic acid (22:6n-3) (RBC EPA+DHA) representing omega 3 fatty acid metabolism and/or intake (Bowman G L et al. (2013) Front Aging Neurosci 5: 92), 2) serum total 25-OH-D encompassing both 25-0H-02 and 25-0H-D3, precursor to 1 α 25-0H-D and regulator of VDR mediated gene expression and dietary exposure (Feart C et al. (2017) Alzheimers Dement 13: 1207-1216; Miller J W et al. (2015) JAMA Neurol 72: 1295-1303; Goodwill A M et al. (2017) J Am Geriatr Soc 65: 2161-2168), 3) plasma total homocysteine as a marker of one-carbon metabolism and indicator of certain B vitamins (B6, 69, B12, betaine) intake (Dayon L et al. (2017) Alzheimers Res Ther 9: 43). Each participants NRI score was a summation of binary coded nutrient biomarkers based on the available literature, including the following definitions for insufficient status: 1) RBC EPA+DHA 5 4.82, (Andrieu S et al. (2017) Lancet Neurol 16: 377-389; Tan Z S et al. (2012) Neurology 78: 658-664; Hooper C et al. (2017) J Nutr Health Aging 21: 988-993) 2) serum vitamin D of 5 20 ng/mL (Feart C et al. (2017) Alzheimers Dement 13: 1207-1216; Ross A C et al. (2011) J Clin Endocrinol Metab 96: 53-58), and 3) plasma homocysteine z 14 μmol/L (Seshadri S et al. (2002) N Engl J Med 346: 476-483). As part of our sensitivity analyses, a "population-based"

approach was used to define nutritional risk using the distribution for each nutrient biomarker observed in the MAPT cohort. This yielded insufficient criteria for lowest quartile of serum vitamin D (≤15 ng/mL) and highest quartile for plasma homocysteine 18.1 μmol/L), while lowest quartile for RBC EPA+DHA remained unchanged.

Statistical Analysis

Descriptive statistics. Insufficient concentrations for each nutrient biomarker for each subject received a point using binary coding. Demographic and clinical characteristic distribution across each nutrient biomarker are compared to identify potential effect modifiers and across the primary outcome, the cognitive composite Z scores to identify potential confounders. Distribution of each nutrient biomarker is presented as histograms with x axis representing the biomarker concentration and y axis representing frequency of each respective concentration. Stacked histograms by the identified effect modifiers are presented (i.e. gender, APOE4 genotype).

Analytical approach and hypothesis testing. We used linear mixed-effects models to evaluate the relationship between baseline NRI scores and rates of change in the cognitive composite Z score over the 3 years in approximately participants that underwent nutrient biomarker analysis. We initially evaluated the relationship between the NRI scores with changes in cognitive composite Z scores under the assumption that the magnitude of the effect estimates on change in cognitive function as a function of each nutrient biomarker were homogeneous. Therefore, any of the biomarkers 1 could contribute, but only one could met insufficient criteria for a NRI of 1 and any 2 for a NRI of 2. Then we evaluated the relationship between the NRI scores and change in cognition under the assumption that the effects were heterogeneous and rather depend on the specific nutritional biomarker or the distinct nutritional biomarker combination that constitutes the NRI score. This approach yielded 8 distinct NRI scores where NRI of 0 and NRI of 3 remain unchanged, representing without or maximum nutritional risk, respectively. A NRI of 1 yielded three possible nutritional risk profiles, one for each nutritional biomarker judged insufficient. A NRI of 2 yielded three possible nutritional risk profiles. Each of the mixed-models were adjusted for baseline age, gender, education (years), and trial arm (model 1) with intercept and slope as random effects. We further adjusted for APOE4 carrier status and baseline CDR (model 2). There were two approaches to examine the sensitivity of our primary results: 1) used population-based criteria (quartiles) for the binary coding of cutoffs for each nutritional biomarker that constituted each NRI score, and 2) restricted the analysis of the NRI to participants naïve to the omega 3 supplementation (placebo only and placebo plus the multi-domain intervention arms only).

Example 2

The following non-limiting example is illustrative of compositions for attenuating cognitive ageing in a non-demented individual, in embodiments provided by the present disclosure.

| Ingredient | Dose/Day |
|---|---|
| DHA | 770 mg |
| EPA | 700 mg |
| Vitamin B1 (thiamin) | 50 mg |
| Vitamin B2 (riboflavin) | 15 mg |

US 12,576,102 B2

41

-continued

| Ingredient | Dose/Day |
|---|---|
| Vitamin B3 (niacin) | 25 mg |
| Vitamin B5 (pantothenic acid) | 23 mg |
| Vitamin B6 (pyridoxine) | 18 mg |
| Vitamin B7 (biotin) | 0.15 mg |
| Vitamin B9 (folic acid anhydrous) | 0.4 mg |
| Vitamin B12 (cobalamin) | about 12 to 21 times RDA of Vit B12 |
| Vitamin C | 500 mg |
| Vitamin D | 0.015 mg |
| Vitamin E | 82.6 mg |
| Selenium | 0.08 mg |
| Citrulline | 3000 mg |
| Choline bitartrate | 85 mg |

All publications mentioned in the above specification are herein incorporated by reference. Various modifications and variations of the disclosed agents, compositions, uses and methods of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A method for identifying pre-disposition to cognitive decline in a subject, the method comprising:

calculating a Nutritional Risk Index (NRI) of the subject, wherein the calculating the NRI of the subject comprises:

(a) obtaining an erythrocyte sample from the subject and determining a level of eicosapentaenoic acid (EPA) and docosahexaenoic acid (DHA) in the erythrocyte sample, wherein the level of EPA and DHA of less than or equal to about 4.82 weight percent of total fatty acids in the erythrocyte sample from the subject is assigned a score of n, and the level of EPA and DHA of more than about 4.82 weight percent of total fatty acids in the erythrocyte sample from the subject is assigned a score of zero;

(b) obtaining a serum sample from the subject and determining a level of 25-hydroxyvitamin D in the serum sample, wherein the level of 25-hydroxyvitamin D in the serum sample from the subject that is less than or equal to about 15 ng/ml is assigned a score of n, and the level of 25-hydroxyvitamin D in the serum sample from the subject that is more than about 15 ng/ml is assigned a score of zero; and (c) obtaining a plasma sample from the subject and determining a level of homocysteine in the plasma sample, wherein the level of homocysteine in the plasma sample from the subject that greater than or equal to about 18.1 μmol/L is assigned a score of n, and the level of homocysteine in the plasma sample from the subject that is lower than about 18.1 μmol/L is assigned a score of zero, wherein n is a positive integer, wherein the NRI of the subject is calculated as the sum of scores obtained from steps (a), (b) and/or (c), and an NRI score greater than zero is indicative of pre-disposition to cognitive decline of the subject.

2. The method of claim 1, wherein the 25-hydroxyvitamin D is selected from the group consisting of 25-hydroxyvitamin D3 and 25-hydroxyvitamin D2.

3. The method of claim 1, wherein the subject is selected from the group consisting of a human subject and companion animal subject.

4. The method of claim 1, wherein the determining the level of vitamin D in the serum sample comprises using electrochemiluminescence.

5. The method of claim 1, wherein the determining the level of homocysteine in the plasma sample comprises using an enzymatic cycling assay.

6. The method of claim 1, wherein the determining the level of EPA and DHA acids in the erythrocyte sample comprises using gas chromatography coupled with a flame ionization detector.

7. The method of claim 1, wherein the obtaining the erythrocyte sample comprises obtaining a plasma sample from the subject and separating erythrocytes from the plasma by centrifugation.

8. The method of claim 1, wherein the NRI score is calculated independent of age, gender, education, and APOE4 genotype.

9. The method of claim 1, wherein the EPA and DHA are both erythrocyte membrane EPA and erythrocyte membrane DHA.

10. The method of claim 1, wherein the subject does not have dementia.

11. The method of claim 1, wherein the subject has at least one risk factor selected from the group consisting of: a Clinical Dementia Rating (CDR) of 0.5, a risk score in Cardiovascular Risk Factors, Aging and Dementia (CAIDE) of 10 to 15, amyloid positive on amyloid PET scans, and a genotype indicating risk of dementia.

* * * * *